(12) United States Patent
Ahn et al.

(10) Patent No.: US 12,408,866 B2
(45) Date of Patent: Sep. 9, 2025

(54) WEARABLE DEVICE FOR IDENTIFYING BREATHING STATE OF USER

(71) Applicant: Samsung Electronics Co., Ltd., Suwon-si (KR)

(72) Inventors: Joongwoo Ahn, Suwon-si (KR); Younghyun Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 556 days.

(21) Appl. No.: 17/874,856

(22) Filed: Jul. 27, 2022

(65) Prior Publication Data

US 2023/0128404 A1 Apr. 27, 2023

Related U.S. Application Data

(63) Continuation of application No. PCT/KR2022/010725, filed on Jul. 21, 2022.

(30) Foreign Application Priority Data

Oct. 25, 2021 (KR) .......................... 10-2021-0142478
Nov. 22, 2021 (KR) .......................... 10-2021-0161793

(51) Int. Cl.
*A61B 5/00* (2006.01)
*A61B 5/0205* (2006.01)
(Continued)

(52) U.S. Cl.
CPC .......... *A61B 5/6803* (2013.01); *A61B 5/0205* (2013.01); *A61B 5/0816* (2013.01);
(Continued)

(58) Field of Classification Search
CPC ... A61B 5/6803; A61B 5/0205; A61B 5/7445; A61B 7/003; A61B 5/02416; A61B 2562/0204; A61B 5/4818
See application file for complete search history.

(56) References Cited

U.S. PATENT DOCUMENTS

| 9,144,405 B2 | 9/2015 | Kim et al. |
| 10,178,969 B2 | 1/2019 | Anwar et al. |

(Continued)

FOREIGN PATENT DOCUMENTS

| KR | 10-1042780 B1 | 6/2011 |
| KR | 10-2014-0039452 A | 4/2014 |

(Continued)

OTHER PUBLICATIONS

International Search Report with English translation and Written Opinion dated Nov. 8, 2022; International Appln. No. PCT/KR2022/010725.

*Primary Examiner* — Catherine M Voorhees
(74) *Attorney, Agent, or Firm* — Jefferson IP Law, LLP

(57) ABSTRACT

A wearable device is provided. The wearable device includes a memory configured to store instructions, at least one display having a display area, a frame configured to support the at least one display, the frame including a nose pad in contact with a part of a user's body wearing the wearable device, a photoplethysmography (PPG) sensor exposed through at least a portion of the frame in contact with other part of the user's body, at least one microphone disposed in the nose pad, and a processor. The processor, when executing the instructions, is configured to identify a breathing state of the user, based at least in part on first data acquired through the PPG sensor and second data acquired through the at least one microphone.

20 Claims, 15 Drawing Sheets

(51) Int. Cl.
*A61B 5/08* (2006.01)
*A61B 7/00* (2006.01)
*H04R 1/08* (2006.01)
*H04R 3/00* (2006.01)
*A61B 5/024* (2006.01)

(52) U.S. Cl.
CPC .......... *A61B 5/7203* (2013.01); *A61B 5/7285* (2013.01); *A61B 5/7445* (2013.01); *A61B 7/003* (2013.01); *H04R 1/08* (2013.01); *H04R 3/00* (2013.01); *A61B 5/02416* (2013.01); *A61B 5/0826* (2013.01); *A61B 2562/0219* (2013.01); *H04R 2499/15* (2013.01)

(56) References Cited

U.S. PATENT DOCUMENTS

| | | |
|---|---|---|
| 11,231,907 B2 | 1/2022 | Heo |
| 11,645,821 B2 | 5/2023 | Uhm et al. |
| 2016/0081651 A1 | 3/2016 | Nam et al. |
| 2017/0095215 A1* | 4/2017 | Watson ................ A61B 5/0002 |
| 2017/0188947 A1* | 7/2017 | Connor ................ A61B 5/369 |
| 2018/0078187 A1* | 3/2018 | Anwar ................ A61B 5/369 |
| 2018/0092547 A1* | 4/2018 | Tzvieli ................ A61B 5/0816 |
| 2018/0317846 A1* | 11/2018 | Moyerman .......... A61B 5/6803 |
| 2019/0028789 A1* | 1/2019 | Stockton, X ........ H04R 1/1058 |
| 2021/0109352 A1 | 4/2021 | Lee et al. |
| 2021/0386318 A1* | 12/2021 | Rahman ................ A61B 5/7285 |
| 2024/0041401 A1* | 2/2024 | Reinhart ................ A61B 5/6815 |

FOREIGN PATENT DOCUMENTS

| | | |
|---|---|---|
| KR | 10-2019-0121720 A | 10/2019 |
| KR | 10-2020-0048407 A | 5/2020 |
| KR | 10-2020-0064774 A | 6/2020 |
| KR | 10-2021-0042746 A | 4/2021 |
| KR | 10-2462678 B1 | 11/2022 |
| WO | 2016/194772 A1 | 12/2016 |

\* cited by examiner

WEARABLE DEVICE FOR IDENTIFYING BREATHING STATE OF USER

CROSS-REFERENCE TO RELATED APPLICATION(S)

This application is a continuation application, claiming priority under § 365 (c), of an International application No. PCT/KR2022/010725, filed on Jul. 21, 2022, which is based on and claims the benefit of a Korean patent application number 10-2021-0142478, filed on Oct. 25, 2021, in the Korean Intellectual Property Office, and of a Korean patent application number 10-2021-0161793, filed on Nov. 22, 2021, in the Korean Intellectual Property Office, the disclosure of each of which is incorporated by reference herein in its entirety.

BACKGROUND

1. Technical Field

The disclosure relates to a wearable device for identifying a breathing state of its user.

2. Description of Related Art

For identifying a user's breathing state, an electronic device may include a photoplethysmography (PPG) sensor or a microphone. The PPG sensor can emit light into the user's body and receive reflected light of the emitted light, thereby identifying a change in blood vessel volume caused by a user's respiration. The PPG sensor may identify the user's respiration through the change in the blood vessel volume. A microphone may be positioned around the user's nose to identify audio signals due to vibrations of air flowing through the user's nasal passages. The microphone may identify the user's breathing through identification of the audio signals.

The wearable device may be used being worn on a part of a user's body. The wearable device may be provided in various types of products in use. For example, the wearable device may be commonly a glasses-type of device that provides its user with augmented reality (AR) or virtual reality (VR).

When the wearable device is worn by a user, the wearable device may be in contact with or adjacent to a part of the user's body. The wearable device may include a PPG sensor or a microphone to identify a user's breathing state. The PPG sensor may have a feature of using relatively low power consumption, but it may have reduced accuracy to identify the user's breathing state because it is usually required to detect reflected light to emitted light. The microphone may have relatively high accuracy in identifying the user's breathing state, but it consumes relatively higher power, so a power consumption efficiency of the wearable device may decrease. Thus, in order for such a wearable device to operate for an extended time duration while being worn on a part of the user's body, it may require more efficient power consumption scheme.

Various embodiments of the disclosure can obtain biometric data including a user's heart rate by means of a PPG sensor and switch the microphone to an active state when an abnormality is detected based on the obtained data, thereby enabling an accurate identification of the user's breathing state.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a wearable device for identifying a breathing state of its user.

Additional aspects will be set forth in part in the description which follows and, in part, will be apparent from the description, or may be learned by practice of the presented embodiments.

In accordance with an aspect of the disclosure, a wearable device is provided. The wearable device includes a memory configured to store instructions, at least one display configured to transmit light directed to a first surface through a second surface, the second surface facing opposite to the first surface, the at least one display including a display area on the first surface or the second surface, a frame configured to support the at least one display, the frame including a nose pad in contact with a part of a user's body wearing the wearable device, a photoplethysmography (PPG) sensor exposed through at least a portion of the frame in contact with other part of the user's body, at least one microphone disposed in the nose pad, and a processor. The processor, when executing the instructions, is configured to identify a breathing state of the user, based at least in part on first data obtained through the PPG sensor or second data obtained through the at least one microphone.

In accordance with another aspect of the disclosure, a wearable device is provided. The wearable device includes a memory configured to store instructions, at least one display configured to transmit light directed to a first surface through a second surface, the second surface facing opposite to the first surface, the at least one display including a display area on the first surface or the second surface, a frame configured to support the at least one display, the frame including a nose pad, a PPG sensor exposed through at least a portion of the frame, at least one microphone disposed in the nose pad, and a processor. The processor, when executing the instructions, is configured to acquire a PPG signal through the PPG sensor while the at least one microphone is in an inactive state, acquire biometric data of a user wearing the wearable device, based on the PPG signal, switch a state of the at least one microphone from the inactive state to an active state, based on identifying that the biometric data corresponds to reference data, acquire audio signals through the at least one microphone switched to the active state, and identify a breathing state of the user based on the audio signals.

According to various embodiments of the present disclosure, the wearable device can use a PPG sensor to obtain biometric data including the user's heart rate, thereby consuming relatively less power to identify abnormalities in the user's breathing. The wearable device, when an abnormal symptom is identified, can activate a microphone to identify the user's breathing state, thereby improving efficiency of its power consumption. The PPG sensor and the microphone of the wearable device may be disposed at a position where it is easy to obtain data related to the user's breathing, while the wearable device is worn by the user. The wearable device can provide the user with a notification to continuously monitor the user's health condition, when the user's breathing state is in a designated state.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
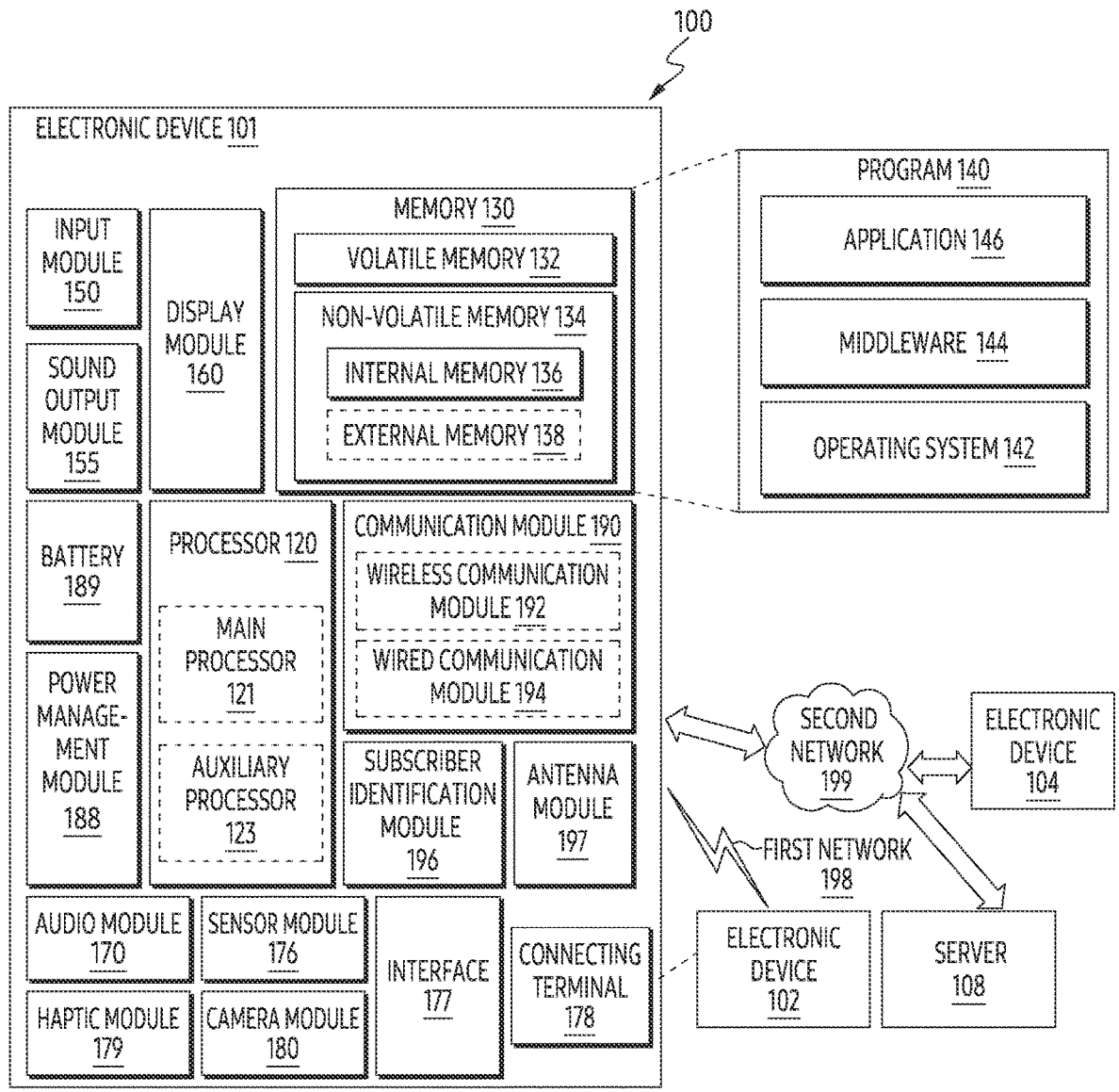
FIG. 1 is a block diagram of an electronic device in a network environment according to an embodiment of the disclosure.

FIG. 1 is a block diagram of an electronic device in a network environment according to an embodiment of the disclosure.

Referring to FIG. 1, an electronic device 101 in a network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, a memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high-definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a $5^{th}$ generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a $4^{th}$ generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to address, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element including a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to certain embodiments, the antenna module 197 may be a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra-low latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
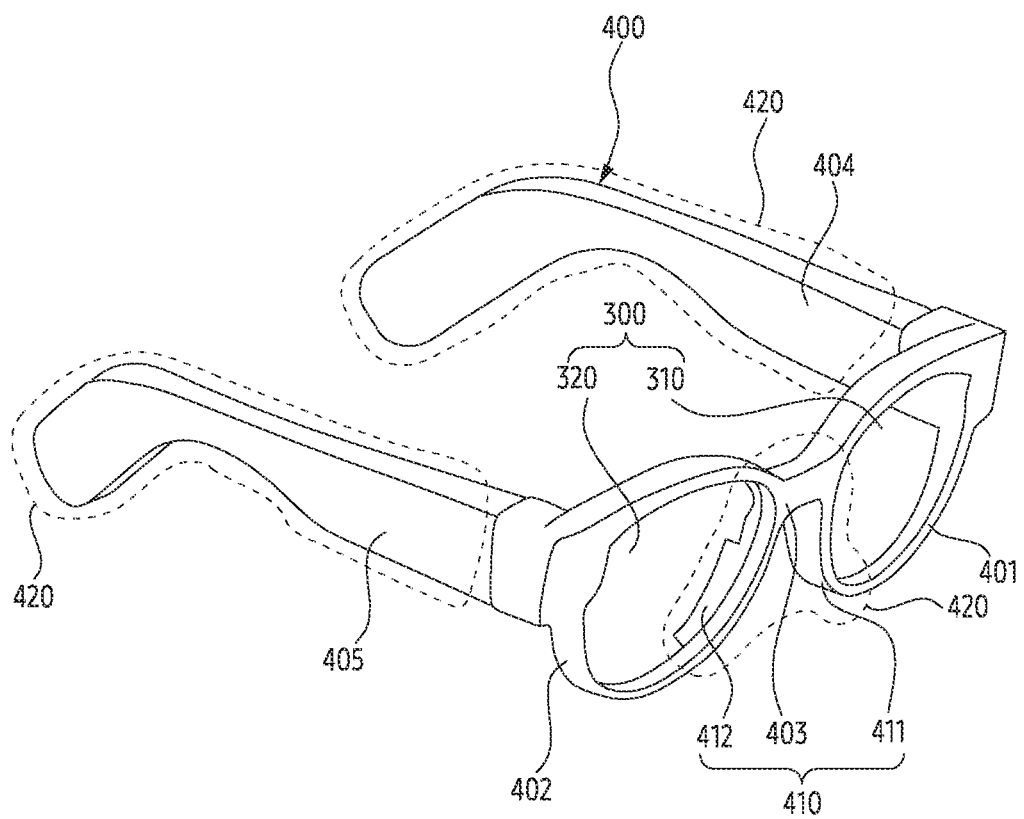
FIG. 2A is a perspective view of an electronic device according to an embodiment of the disclosure.
Figure 2B:
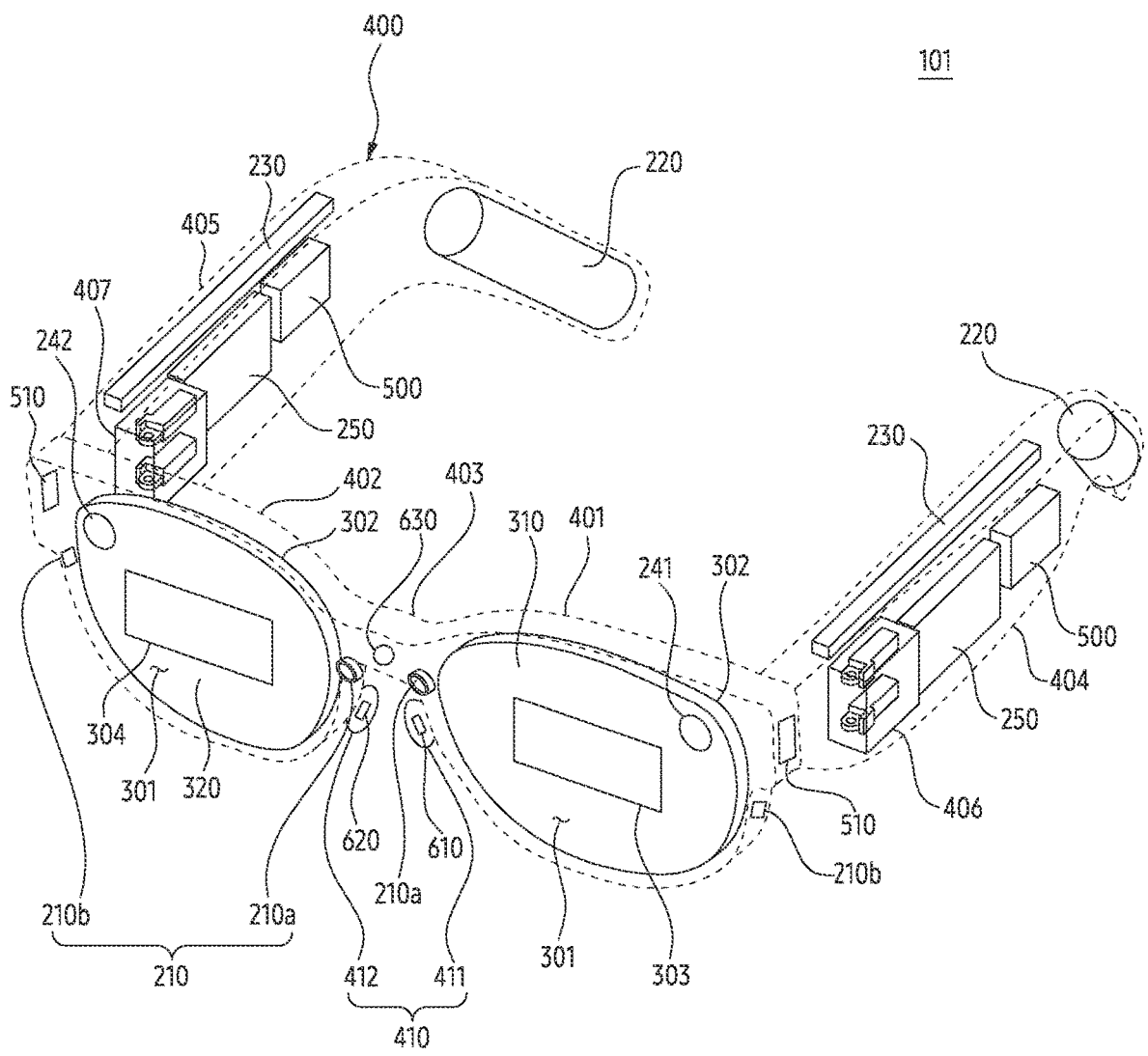
FIG. 2B is a schematic diagram showing an example of arrangements of electronic components in an electronic device according to an embodiment of the disclosure.

FIG. 2A is a perspective view of an electronic device according to an embodiment of the disclosure. FIG. 2B is a schematic diagram showing an example of arrangements of electronic components included in the electronic device according to an embodiment of the disclosure.

Referring to FIGS. 2A and 2B, an electronic device (e.g., an electronic device 101 of FIG. 1) may include a memory (e.g., a memory 130 of FIG. 1) configured to store instructions, at least one display 300, a frame 400 supporting the at least one display 300, a photoplethysmography (PPG) sensor acquiring first data, at least one microphone 600 acquiring second data, and a processor (e.g., a processor 120 of FIG. 1) configured to identify a user's breathing state.

According to an embodiment, the electronic device 101 may be referred to as a wearable device that is worn on a portion of a user's body. The electronic device 101 may provide a user wearing the electronic device 101 with augmented reality (AR), virtual reality (VR), or mixed reality (MR) in which augmented reality and virtual reality are mixed together. For example, the electronic device 101 may display on the at least one display 300 a virtual reality image provided from at least one optical devices 241 and 242, in response to a user's designated gesture obtained through a motion recognition camera 210*b*.

According to an embodiment, the memory may store instructions executed by the processor. The instructions stored in the memory may be related to a designated function of the electronic device 101. For example, the memory may store instructions related to the operation of the PPG sensor 500 and the at least one microphone 600. When the instruction is loaded by the processor, the processor may control the electronic device 101 to perform an operation designated in the instruction.

According to an embodiment, the at least one display 300 may provide visual information to the user. For example, the at least one display 300 may include a transparent or translucent lens. The at least one display 300 may include a first display 310 and/or a second display 320 spaced apart from the first display 310. For example, the first display 310 and the second display 320 may be disposed at positions each corresponding to the left and right eyes of the user.

Referring to FIG. 2B, the at least one display 300 may provide visual information transmitted from external light to the user through a lens included in the at least one display 300, and other visual information distinct from the visual information. For example, the at least one display 300 may include a first surface 301 and a second surface 302, the second surface 302 being disposed opposite to the first surface 301, and may have a display area on the second surface 302. When the user wears the electronic device 101, external light may be incident onto the first surface 301, and transmitted through the second surface 302 to the user's eyes. For another example, the at least one display 300 may display, on a display area on the second surface 302, an augmented reality (AR) image in which a virtual reality (VR) image projected from the at least one optical device 241 and 242 is combined with a real image screen transmitted through the external light. The at least one display 300 may include at least one waveguide 303 and 304 adapted to diffract light output from the at least one optical device 241 and 242 and transmit it to the user. The electronic device 101 may analyze an object included in a real image collected through an imaging camera (not shown), and combine thereto a virtual object corresponding to an object to be provided with augmented reality of the analyzed objects, for displaying the virtual object on at least one display 300. The virtual object may include at least one of text or an image for various information related to the object included in the real image. Then, the user wearing the electronic device 101 may view an image displayed on the at least one display 300.

According to an embodiment, the frame 400 may be implemented with a physical structure in which the electronic device 101 can be worn on a user's body. According to an embodiment, the frame 400 may be configured such that, when the user wears the electronic device 101, the first display 310 and the second display 320 may be disposed to correspond to the left eye and the right eye of the user, respectively.

The frame 400 may be configured to support the at least one display 300. For example, the frame 400 may support the first display 310 and the second display 320 to be disposed at positions corresponding to the user's left and right eyes.

Referring to FIG. 2A, when the user wears the electronic device 101, the frame 400 may include a region 420 in which at least a portion comes into contact with a part of the user's body. For example, the region 420 of the frame 400 that comes into contact with a part of the user's body may include a part of the user's nose, a part of the user's ear, and a side part of the user's face with which the electronic device 101 is in contact. According to an embodiment, the frame 400 may include a nose pad 410 that is in contact with a part of the user's body. When the electronic device 101 is worn by the user, the nose pad 410 may be in contact with a part of the user's nose. The frame 400 may include a first temple 404 and a second temple 405 that are in contact with another part of the user's body, which is distinct from the aforementioned part of the user's body.

For example, the frame 400 may include a first rim 401 surrounding at least a portion of the first display 310, a second rim 402 surrounding at least a portion of the second display 320, a bridge 403 disposed between the first rim 401 and the second rim 402, a first pad 411 disposed along a portion of an edge of the first rim 401 from one end of the bridge 403, a second pad 412 disposed along a portion of an edge of the second rim 402 from the other end of the bridge 403, the first temple 404 extending from the first rim 401 and secured to a portion of the wearer's ear, and the second temple 405 extending from the second rim 402 and secured to a portion of the wearer's opposite ear. The first pad 411 and the second pad 412 may come into contact with a portion of the user's nose, and the first temple 404 and the second temple 405 may be in contact with a portion of the user's face and a portion of the ear. The temples 404, 405 may be rotatably connected to the rims via hinges 406 and 407, respectively. The first temple 404 may be rotatably connected to the first rim 401 through a first hinge 406 disposed between the first rim 401 and the first temple 404. Likewise, the second temple 405 may be rotatably connected to the second rim 402 through a second hinge 407 disposed between the second rim 402 and the second temple 405.

According to an embodiment, the PPG sensor 500 may obtain first data related to the user's respiration. The first data may include a heart rate, a change in the user's heart rate per unit time, oxygen saturation, and/or blood pressure, which may be identified from the PPG signal. The PPG sensor 500 may obtain biometric data on a change in blood flow in a microvasculature, using light. The PPG sensor 500 may obtain the first data by making contact with a body part (e.g., a finger, an ankle, a wrist, an ear, a face, and so on) of the user. In response to repeated contractions and relaxations of the heart, the blood flow rate of peripheral blood vessels may change, and the volume of the blood vessels may change due to the change in the blood flow rate. The PPG sensor 500 may obtain the first data by measuring a change in the volume of the blood vessel accruing from an increase and/or a decrease in the blood flow rate within the blood vessel.

The PPG sensor 500 may emit light into a human tissue and receive reflected light for the emitted light. When the light incident into the tissue is partially absorbed in the tissue, the amount of light absorbed may be changed by the blood flow rate. The reflected light received by the PPG sensor 500 may be subtracted by the amount of light absorbed by the blood vessel. The PPG sensor 500 may identify a user's heart rate, oxygen saturation, and/or blood pressure by acquiring a PPG signal, based on a change in the blood flow rate synchronized with a heartbeat.

The PPG sensor 500 may be exposed through at least a portion of the frame 400 that is in contact with another part of the user's body. The other part of the user's body may be distinguished from a part of the user's body with which the nose pad 410 is in contact. For example, when the electronic device 101 is worn by the user, the nose pad 410 may be in contact with the part of the user's nose, and the PPG sensor 500 may be exposed through the temples 404 and 405 in contact with a part of the user's face and a part of the user's ear. The PPG sensor 500 may emit light to another part of the user's body and obtain reflected light with respect to the emitted light, thereby obtaining the first data that can be used to identify information on respiration, heart rate, oxygen saturation and/or blood pressure for a user wearing the electronic device 101.

According to an embodiment, the at least one microphone 600 may obtain second data about the user. The second data may include at least one audio signal generated from a part of the user's body. The at least one microphone 600 may be disposed in the nose pad 410 in contact with a part of the user's body. When the electronic device 101 is worn by the user, the nose pad 410 may be adjacent to the user's nose. The at least one microphone 600 disposed within the nose pad 410 may identify vibrations and/or sounds caused by air passing through the user's nasal cavity. For example, the at least one microphone 600 may obtain a breathing sound generated by the user's breathing, and identify an audio signal from the breathing sound. With the second data in direct association with the user's breathing, it is possible to identify the user's breathing state. For example, it is possible to identify the user's breathing state, through an intensity of the at least one audio signal, an interval of the signals, a change in the signals, and/or a period of the signal, which are included in the second data.

According to an embodiment, a processor may be referred to as the processor above-mentioned with reference to FIG. 1. According to an embodiment, the processor may be mounted on a printed circuit board 250 incorporated into the electronic device 101. The processor may execute instructions stored in the memory to control the overall operation of the electronic device 101.

The processor may be connected to the PPG sensor 500 and at least one microphone 600. The processor may be operatively connected or electrically connected to the PPG sensor 500 and the at least one microphone 600, so as to receive data from the PPG sensor 500 and the at least one microphone 600 or control the operation of the PPG sensor 500 and the at least one microphone 600 as required. For example, the processor may receive the first data obtained through the PPG sensor 500 and the second data obtained through the at least one microphone 600. The processor may transmit designated signals to the PPG sensor 500 and the at least one microphone 600.

The processor may be configured to identify a breathing state of the user, based at least in part on the first data obtained through the PPG sensor 500 and the second data obtained through the at least one microphone 600. For example, the processor may identify an abnormal respiration of the user with the first data, and may identify the user's breathing state with the second data. For example, when a change in the user's heart rate per a unit time included in the first data is rapidly made, the processor may detect an abnormal respiration of the user, and precisely identify the user's state of respiration using the audio signal included in the second data.

According to an embodiment, the electronic device 101 may include various electronic components for performing various functions. For example, the various electronic components may include a battery module 220, an antenna module 230, at least one optical device 241 and 242, a sound output module (not shown), a light emitting module (not shown), and/or a printed circuit board 250. The various electronic components may be disposed in the frame 400 to perform a designated function, respectively.

According to an embodiment, the at least one optical device 241 and 242 may project a virtual object on the at least one display 300 in order to provide various image information to the user. For example, the at least one optical device 241 and 242 may be a projector. The at least one optical device 241 and 242 may be disposed adjacent to the at least one display 300 or may be provided as a part of the at least one display 300. According to an embodiment, the electronic device 101 may include a first optical device 241 corresponding to the first display 310 and a second optical device 242 corresponding to the second display 320. For example, the at least one optical device may include a first optical device 241 disposed on an edge of the first display 310 and a second optical device 242 disposed on an edge of the second display 320. The first optical device 241 may transmit light to a first waveguide 303 disposed on the first display 310, and the second optical device 242 may transmit light to a second waveguide 304 disposed on the second display 320.

According to various embodiments, the camera 210 may include an imaging camera, an eye tracking camera (ET CAM) 210a, and/or a motion recognition camera 210b. The imaging camera, the eye tracking camera 210a, and the motion recognition camera 210b may be disposed at different positions on the frame 400 and may perform different functions.

The imaging camera may capture an actual image or background to be matched with a virtual image in order to implement augmented reality or mixed reality contents. The imaging camera may capture an image of a specific object existing at a position viewed by the user, and provide the image to the at least one display 300. The at least one display 300 may display information about the actual image or background including the image of the specific object obtained using the imaging camera, and an image superimposed with a virtual image provided through the at least one optical device 241 and 242. According to an embodiment, the imaging camera may be disposed on a bridge 403 disposed between the first rim 401 and the second rim 402.

The eye tracking camera 210a may track a gaze of the user wearing the electronic device 101, thereby matching the user's gaze with the visual information provided to the at least one display 300 to implement more realistic augmented reality. For example, when the user looks at the front, the electronic device 101 may naturally display environment information covering the front of the user at the place where the user is located, on the at least one display 300. The eye tracking camera 210a may be configured to capture an image of the user's pupil in order to determine the user's gaze. For example, the eye tracking camera 210a may receive gaze-detected light reflected from the user's pupil, and track the user's gaze based on the position and movement of the received gaze-detected light. According to an embodiment, the eye tracking camera 210a may be disposed at positions corresponding to the user's left and right eyes. For example, the eye tracking camera 210a may be arranged within the first rim 401 and/or the second rim 402 to face a direction in which the user wearing the electronic device 101 is positioned.

The motion recognition camera 210b may recognize a movement of a whole body or part of the user such as e.g., the user's torso, hands, or face to provide a specific event to a screen provided on the at least one display 300. The motion recognition camera 210b may obtain a signal corresponding to the motion by recognizing the user's gesture, and may provide a display corresponding to the signal on the at least one display 300. The processor may identify the signal corresponding to the motion, and perform a designated function based on the identification. According to an embodiment, the motion recognition camera 210b may be disposed on the first rim 401 and/or the second rim 402.

According to an embodiment, the battery module 220 may supply power to electronic components of the electronic device 101. This battery module 220 may be, for instance, referred to as the battery 189 shown in FIG. 1. According to an embodiment, the battery module 220 may be disposed in the first temple 404 and/or the second temple 405. For example, the battery module 220 may include a plurality of battery modules 220. The plurality of battery modules 220 may be disposed in the first temple 404 and/or the second temple 405, respectively. According to an embodiment, the battery module 220 may be arranged at one end of the first temple 404 and/or the second temple 405.

The antenna module 230 may transmit a signal or power to the outside of the electronic device 101, or may receive a signal or power from the outside. This antenna module 230 may be referred to as the antenna module 197 of FIG. 1. According to an embodiment, the antenna module 230 may be disposed in the first temple 404 and/or the second temple 405. For example, the antenna module 230 may be arranged in vicinity of one surface of the first temple 404 and/or the second temple 405.

The sound output module (not shown) may output a sound signal to the outside of the electronic device 101. This sound output module may be referred to as the sound output module 155 of FIG. 1. According to an embodiment, the sound output module may be disposed in the first temple 404 and/or the second temple 405 to be arranged more adjacent to ears of the user wearing the electronic device 101. For example, the sound output module may include a first sound output module disposed adjacent to the user's right ear within the first temple 404 and a second sound output module disposed adjacent to the user's left ear within the second temple 405.

The light emitting module (not shown) may include at least one light emitting device. In order to visually provide the user with information about a specific state of the electronic device 101, the light emitting module may emit light of a color corresponding to the specific state or emit light in a motion corresponding to the specific state. For example, when charging is required, the electronic device 101 may emit red light at a certain interval. According to an embodiment, the light emitting module 370 may be arranged on the first rim 401 and/or the second rim 402.

Figure 3:
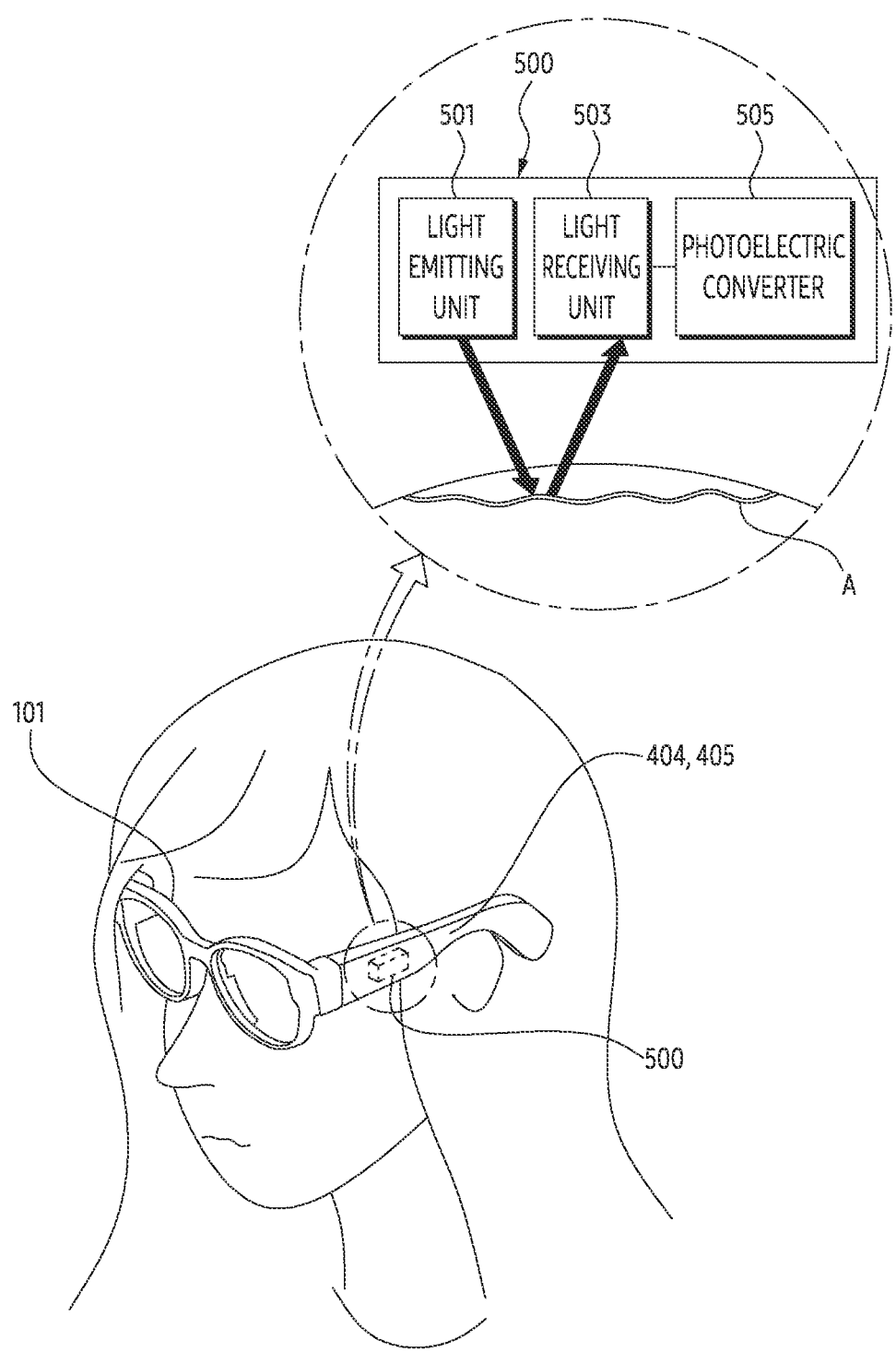
FIG. 3 illustrates an operation of a photoplethysmography (PPG) sensor of an electronic device according to an embodiment of the disclosure.

FIG. 3 illustrates an operation of a PPG sensor of an electronic device according to an embodiment of the disclosure.

Referring to FIG. 3, the PPG sensor 500 may be disposed on the temples 404 and 405 that are in contact with other parts of the user's body. When the electronic device 101 is worn by the user, the temples 404 and 405 may come into contact with a part of a side surface of the user's face and a part of the user's ear. The PPG sensor 500 disposed on the temples 404 and 405 may be exposed toward a side of the user's face or ears. When the user is wearing the electronic device 101, the temples 404 and 405 are adjacent to the user's arteriae temporales, so the PPG sensor 500 disposed on the temple may use the blood flow rate of the user's arteriae temporales to acquire first data.

Referring to FIG. 3, the PPG sensor 500 may include a light emitting unit 501, a light receiving unit 503, and a photoelectric converter 505. According to an embodiment, the light emitting unit 501 may emit light toward the user's body. For example, the light emitting unit 501 may be an LED device emitting light in red and near-infrared wavelength bands that may be easy to penetrate into body tissues. As another example, the light emitting unit 501 may be an LED device emitting light in a green wavelength band with high absorbance in the near-infrared region. The light emitted from the light emitting unit 501 may be absorbed by blood flowing through an artery A located inside the skin.

According to an embodiment, the light receiving unit 503 may identify an amount of reflected light with respect to the emitted light. For example, the light receiving unit 503 may include a photo-sensor (e.g., a photo-diode) to identify the amount of reflected light. The light amount of the reflected light identified by the light receiving unit 503 may be different from the amount of the light emitted from the light emitting unit 501 by the amount of light absorbed in the tissues. The reflected light identified by the light receiving unit 503 may be converted into an electrical signal through the photoelectric converter 505. The electrical signal converted through the photoelectric converter 505 may be represented as a PPG signal. The processor (e.g., the processor 120 of FIG. 1) may acquire, from the PPG signal of the PPG sensor 500, the first data that can be used to identify the user's breathing information, heart rate, oxygen saturation, and/or blood pressure.

The PPG sensor 500 may initiate an operation in response to receiving a designated event. For example, the electronic device 101 may include a wear detection sensor identifying a change in capacitance or a change in impedance, when it is located adjacent to the user's body. In response to identifying that it is worn by the user, the PPG sensor 500 may initiate an action. The PPG sensor 500 may periodically acquire the first data in response to identifying that it is worn by the user. As another example, in order to initiate the operation of the PPG sensor 500, the user may perform a designated gesture, and when the motion recognition camera (e.g., a motion recognition camera 210b in FIG. 2B) recognizes the gesture, the processor (e.g., a processor 120 of FIG. 1) may generate a signal to trigger the operation of the PPG sensor 500. As another example, the electronic device 101 may be provided with an On/Off button related to the operation of the PPG sensor 500, and in response to the user's touching the On/Off button, the processor may generate may generate a signal to trigger the operation of the PPG sensor 500. The processor may receive a request related to initiation of an operation from the external electronic device. For example, the external electronic device may receive the user's input and transmit a request related to triggering the operation of the PPG sensor 500 to the electronic device 101.

Because the amount of power required for the operation of the PPG sensor 500 is relatively low, the PPG sensor 500 may have less power consumption even when the PPG sensor 500 operates for a long time. While the user is wearing the electronic device 101, the PPG sensor 500 may continuously acquire the first data. According to an embodiment, the PPG sensor 500 may be exposed through at least a part of the temples 404 and 405 coming into contact with another part of the user's body wearing the electronic device 101, so the user may not require to separately attach the PPG sensor 500 to a specific position of the body. According to an embodiment, the electronic device 101 may continuously acquire the first data through the PPG sensor 500 merely by being worn by the user.

Figure 4:
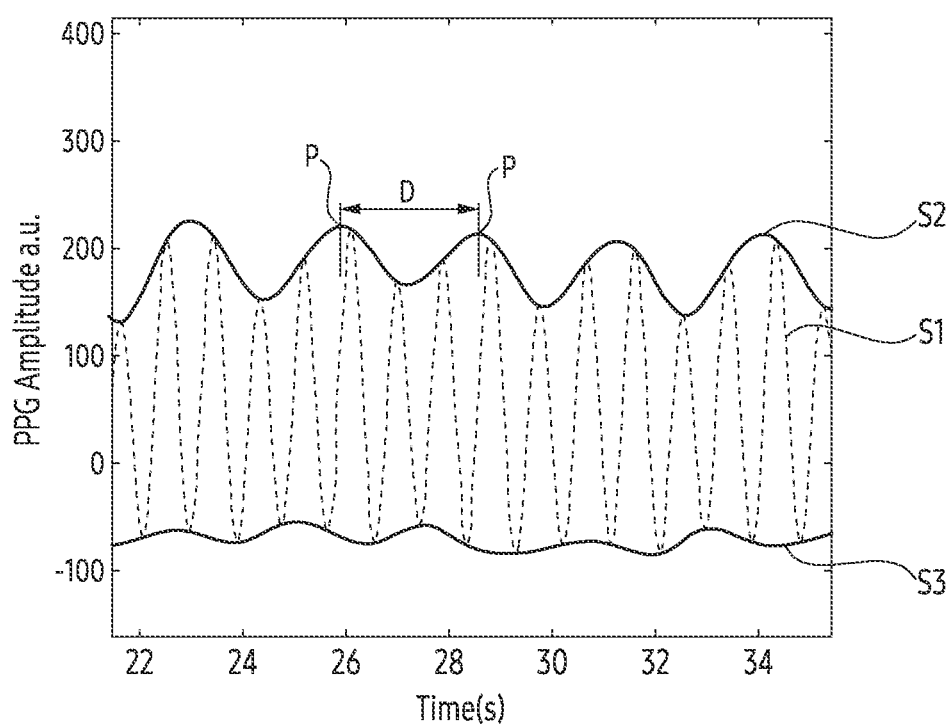
FIG. 4 is a graph of a PPG signal obtained through a PPG sensor of an electronic device according to an embodiment of the disclosure.

FIG. 4 is a graph of a PPG signal obtained through a PPG sensor of an electronic device according to an embodiment of the disclosure.

According to an embodiment, when executing the instructions, the processor (e.g., the processor 120 of FIG. 1) may identify a change in heart rate per unit time of the user through the first data obtained from the PPG sensor (e.g., the PPG sensor 500 of FIG. 2B). Since the PPG sensor may acquire the PPG signal synchronized with a heartbeat, the processor may identify data related to the user's respiration from the PPG signal.

Referring to FIG. 4, the PPG sensor may obtain a graph S1 of the PPG signal converted into an electrical signal. Since the amount of light absorbed in the tissues of the light emitted from the PPG sensor may vary greatly depending on the blood flow rate, the amount of reflected light may relatively decrease in the systole, when the blood flow rate is at the maxim. In the systole, the light receiving unit (e.g., the light receiving unit 503 in FIG. 3) may cause relatively low light absorption to be induced. The amount of reflected light may relatively increase in the diastole, when the blood flow rate is at the minimum. In the diastole, the light receiving unit may cause relatively high light absorption to be induced. From the above-described continuous change in the arterial blood flow, the PPG sensor may obtain the graph S1 of the PPG signal. A graph S2 of the maximum signal of FIG. 4 is a signal obtained by connecting the local maxima values in the graph S1 of the PPG signal, and a graph S3 of the minimum signal of FIG. 4 is a signal obtained by connecting the local minima values in the graph S1 of the PPG signal).

According to an embodiment, the processor may obtain data related to the user's respiration from the graph S1 of the PPG signal, using the correlation between the heart rate and respiration. According to an embodiment, when executing the instructions, the processor may identify the respiration of the user wearing the electronic device (e.g., the electronic device 101 of FIG. 2A) from the graph S2 of the maximum signal and/or the graph S3 of the minimum signal. For example, the processor, when executing the instructions, may measure the time required for the user's one tidal breath, from a time interval D between peaks P of the graph S2 of the maximum value signal. For another example, the processor, when executing the instructions, may measure the user's respiration rate (BRPM, beat rate per minute) from the number of peaks (P) included in the graph S2 of the maximum value for 1 minute. In addition, the processor may obtain various data related to the user's respiration, based on the first data obtained through the PPG sensor.

According to an embodiment, the electronic device may continuously acquire the first data through the PPG sensor 500 while in a state worn by the user. According to an embodiment, the electronic device may identify a heart rate for a unit time of the user from the first data obtained through the PPG sensor 500 and identify a change in the heart rate for a unit time of the user based on the heart rate.

Figure 5:
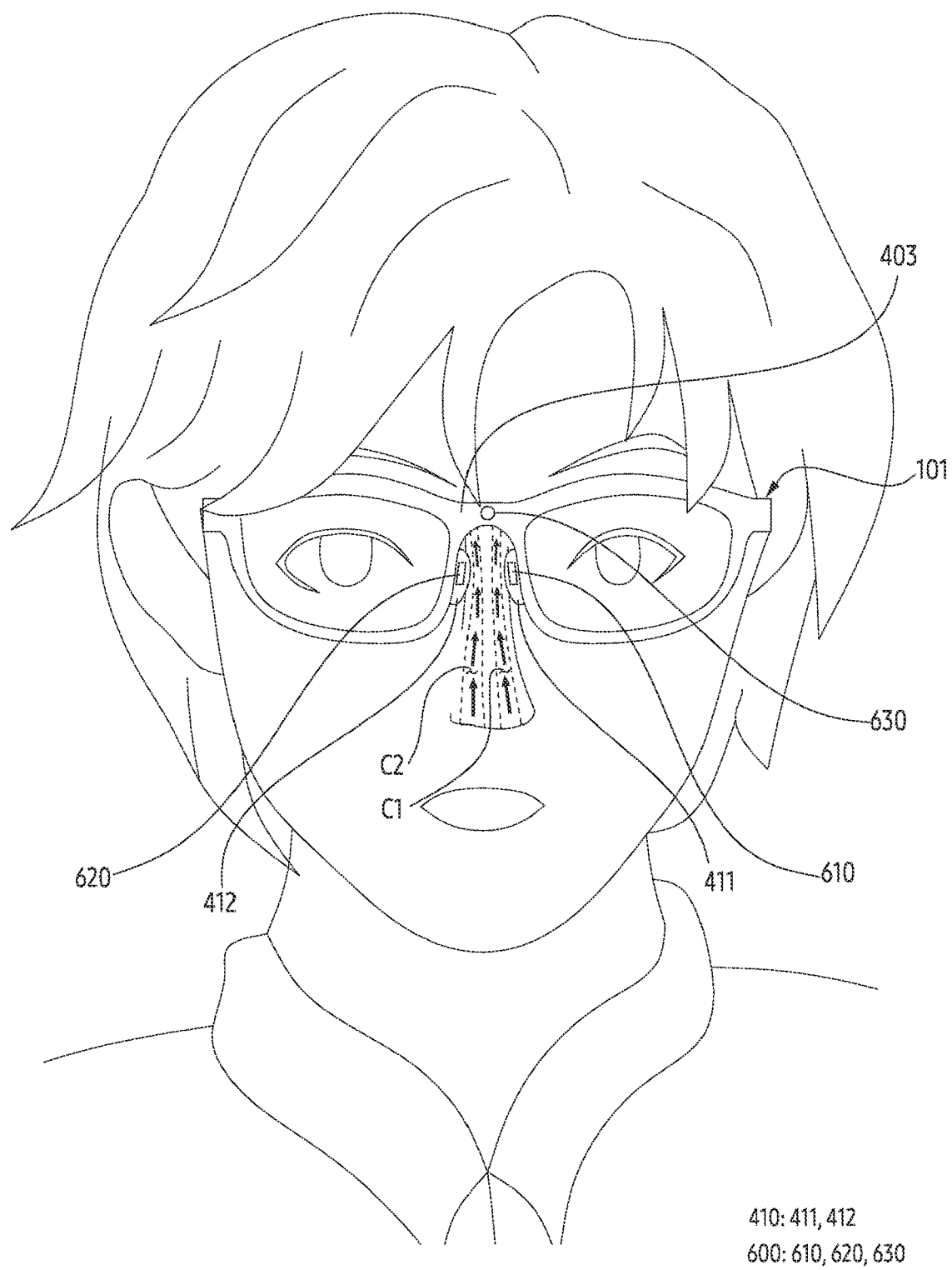
FIG. 5 illustrates at least one microphone of an electronic device according to an embodiment of the disclosure.

FIG. 5 illustrates at least one microphone of an electronic device according to an embodiment of the disclosure.

Referring to FIG. 5, according to an embodiment, the at least one microphone 600 of the electronic device 101 may be disposed within a nose pad 410 that comes into contact with a part of the user's body wearing the wearable device. For example, the nose pad 410 may be disposed on a nose of the user wearing the wearable device, and the at least one microphone 600 may be disposed to face the user's nose within the nose pad 410. The at least one microphone 600 may easily identify audio signals originating from the nose, with the arrangement facing the nose. The at least one microphone 600 may acquire second data for identifying the user's breathing state. When the user wearing the wearable device breathes, air inhaled through the user's nose may flow into the body through the user's nasal cavity. When the air passes through the user's nasal cavity, vibrations and/or sound may occur owing to the flow of air. The at least one microphone 600 may acquire second data through the vibration and/or sound. For example, the at least one microphone 600 may include a diaphragm to capture vibrations caused by user's inspiration and/or expiration, a converter to convert vibrations of the diaphragm into an audio signal, and an amplifier to amplify the audio signal output from the converter. The at least one microphone 600 may acquire at least one audio signal related to the user's breathing sound owing to the arrangement adjacent to the user's nose. When executing the instructions, the processor (e.g., the processor 120 of FIG. 1) may be configured to identify at least one audio signal generated from a part of the user's body among the second data, and based on the at least one audio signal, identify the user's breathing state.

According to an embodiment, the at least one microphone 600 may be a first microphone 610 disposed within the first pad 411 and a second microphone 620 disposed within the second pad 412. The first microphone 610 and the second microphone 620 may be each disposed at positions corresponding to the left nasal cavity C1 and the right nasal cavity C2 of the user. For example, the first microphone 610 may be disposed on the user's left nasal cavity C1 to acquire second data related to the user's left nasal cavity C1, and the second microphone 620 may be disposed on the user's right nasal cavity C2 to acquire second data related to the user's right nasal cavity C2.

According to an embodiment, the processor, when executing the instructions, may acquire the second data through each of the first microphone 610 and the second microphone 620. The processor may distinguish between the second data obtained through the first microphone 610 and the second data obtained through the second microphone 620.

According to an embodiment, the processor may be configured to, when executing the instructions, remove some noise included in the second data to acquire audio signals. Since the at least one microphone 600 converts the vibration transmitted to the diaphragm into an audio signal, the second data obtained from the at least one microphone 600 may include noise due to vibrations caused by unnecessary noise. When the processor executes the instructions, the accuracy of the audio signal of the second data may deteriorate due to noise from the external environment. The processor may remove the noise components included in the second data to improve the accuracy of the audio signal generated from the user's body. For example, according to an embodiment, the electronic device 101 may include a third microphone 630 to acquire audio signals of an external environment and a noise canceling unit. The third microphone 630 may be arranged to face the outside of the electronic device 101 on the bridge 403. The third microphone 630 may identify noise generated in the vicinity of the electronic device 101. The noise canceling unit may analyze the phase of the identified noise and generate a sound wave having an inverse phase of the analyzed phase, thereby cancelling the noise transmitted to the at least one microphone 600. Such cancelling of noise makes it possible for the electronic device 101 to identify an audio signal associated with the user's breathing.

Figure 6:
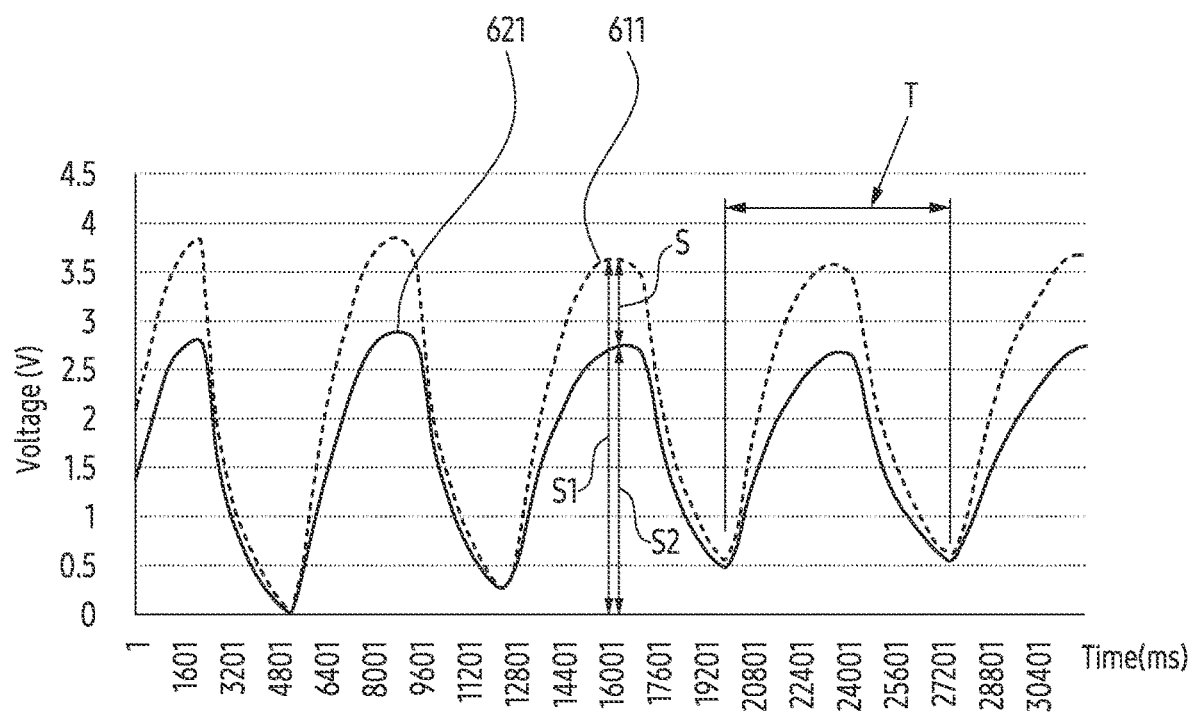
FIG. 6 is a graph of an audio signal obtained through at least one microphone of an electronic device according to an embodiment of the disclosure.

FIG. 6 is a graph of an audio signal obtained through at least one microphone of an electronic device according to an embodiment of the disclosure. The audio signal shown in FIG. 6 may be at least one audio signal generated from a part of the user's body of the second data obtained from at least one microphone (e.g., the microphone 600 of FIG. 2B).

According to one embodiment, through the first microphone (e.g., the first microphone 610 of FIG. 5) and the second microphone (e.g., the second microphone 620 of FIG. 5), the processor may acquire the second data related to the user's left nasal cavity and the second data related to the user's right nasal cavity. The processor (e.g., the processor 120 of FIG. 1) may acquire, when executing the instructions, the second data through each of the first microphone and the second microphone, for a specified time duration from a time point at which each of the first microphone and the second microphone is activated. The processor may identify, through the second data obtained from the at least one microphone, at least one audio signal generated from a part of the body of the user wearing the electronic device (e.g., the electronic device 101 of FIG. 2A). For example, the processor may identify an audio signal associated with a breathing sound originating from the user's nose. The processor may be configured to identify a breathing state of the user based on the identified at least one audio signal.

Referring to FIG. 6, it is shown that there may be a difference in strength between the audio signal 611 obtained from the first microphone and the audio signal 621 obtained from the second microphone. When a person breathes, a volume of respiration through the nasal cavity on both sides may not be uniform for various reasons. For example, for a person whose septum is curved toward one nasal cavity, one nasal cavity is relatively narrower, so the amount of respiration through the other nasal cavity may be greater than that through the one nasal cavity. As another example, due to the nasal cycle in which the contraction and expansion of the nasal mucosa on the both sides alternately occur at a certain time period, a large difference may occur in the respired volumes of both the nasal cavities when a person breathes. As another example, due to a respiratory disease such as e.g., a cold or rhinitis, any one of the nasal cavity might get clogged, so that a person is allowed to breathe only through the other unclogged nasal cavity passage for a certain period of time.

According to an embodiment, the electronic device may acquire the second data through each of the first microphone and the second microphone. The processor, when executing the instructions, may identify the user's breathing state using the audio signal 611 obtained from the first microphone and/or the audio signal 621 obtained from the second microphone.

Referring to FIG. 6, the intensity S1 of the audio signal 611 obtained from the first microphone may be greater than the intensity S2 of the audio signal 621 obtained from the second microphone. In the above, the processor may identify the user's breathing state from the audio signal 611 obtained from the first microphone. The processor, when executing the instructions, may identify the breathing state of the user from the audio signal. For example, when the user inhales, air may be introduced into the body through the nasal cavity, and the intensity of vibrations transmitted to the at least one microphone toward the nasal cavity may increase due to an inflow of the air. An increased intensity of the vibrations may cause an increase in the intensity of the identified audio signal of the second data. When the user exhales, air may flow out of the body through the nasal cavity, and the intensity of vibrations transmitted to the at least one microphone toward the nasal cavity may decrease due to an outflow of the air. Such a decreased intensity of the vibrations may cause a decrease in the intensity of the identified audio signal of the second data.

The processor may identify the user's breathing state through the repetitive increase/decrease in the intensity of the audio signal. For example, the processor may identify the time required for one time of breathing of the user, based on the time T between the points where the electrical signal decreases and increases with the user's respiration. The processor may count the number of increasing/decreasing in the intensity of the signals to identify the user's breathing rate and a change in the breathing rate. The processor may identify a time interval between the inhalation and exhalation and a holding time of each of the inhalation and exhalation, by counting the time of the signal intensity increasing/decreasing. The processor may identify the difference S in breathing intensity in the user's left nasal cavity and right nasal cavity based on the difference between the intensity S1 of the audio signal obtained from the first microphone and the intensity S2 of the audio signal obtained from the second microphone. The processor may identify a time duration of the user's apnea, based on counting the time during which the audio signal generated from a part of the user's body of the second data is not identified. The user's breathing state identifiable by the processor may include one or more of e.g., the user's respiration rate, a change in respiration rate, a holding time of inhalation and exhalation, a time interval between inhalation and exhalation, a difference in breathing intensity between the left and right nasal cavities, and a time duration of the user's apnea, as described above.

Figure 7:
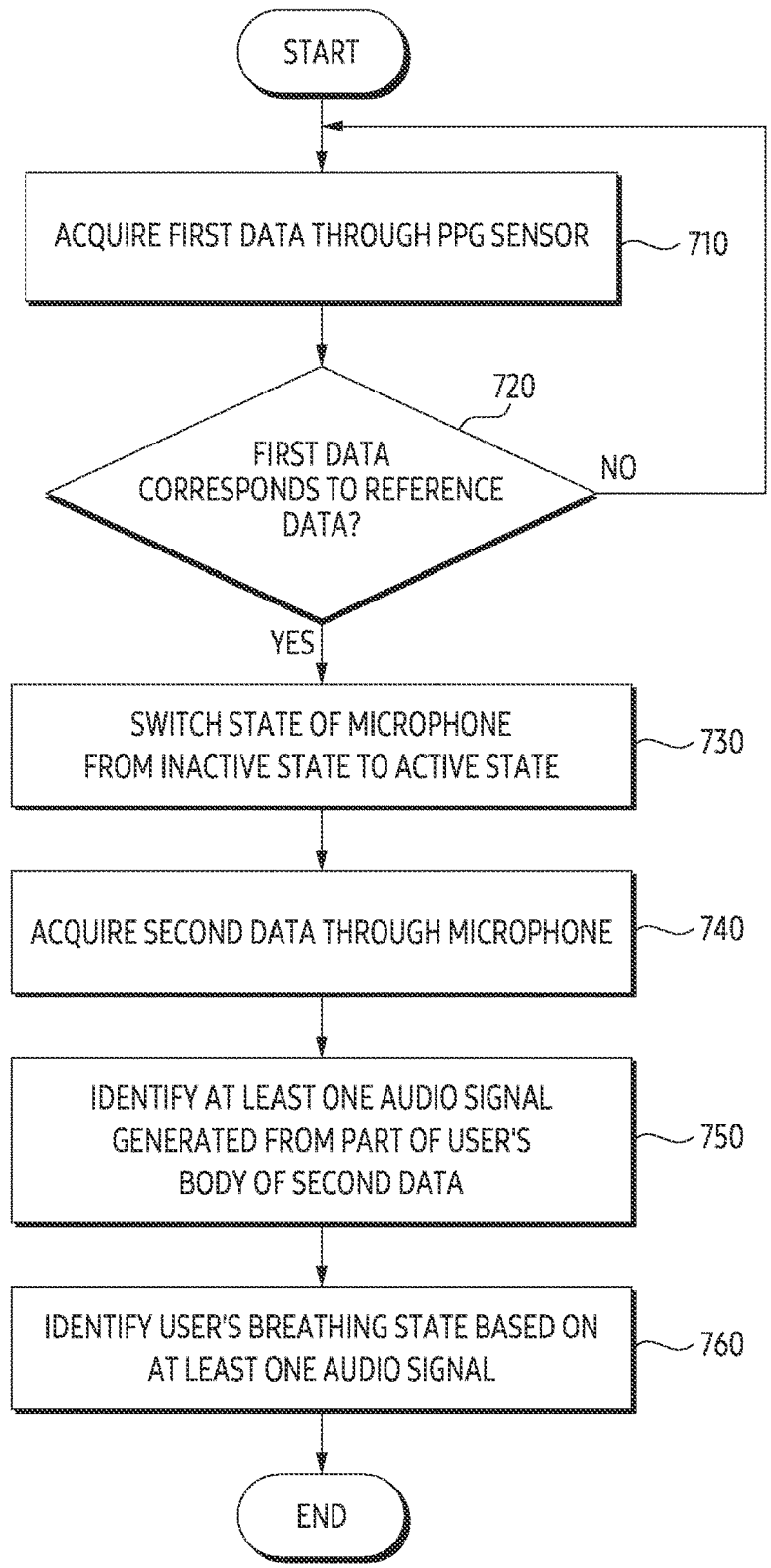
FIG. 7 is a flowchart illustrating an example of operations of a processor of an electronic device according to an embodiment of the disclosure.

FIG. 7 illustrates a flowchart of an example of operation of a processor of an electronic device according to an embodiment of the disclosure.

Referring to FIG. 7, in operation 710, the processor (e.g., the processor 120 of FIG. 1), when executing the instructions, may acquire first data through a PPG sensor (e.g., the PPG sensor 500 of FIG. 2B). The PPG sensor may initiate the operation in response to receiving a designated event. The PPG sensor may emit light into the skin of a user wearing an electronic device (e.g., the electronic device 101 of FIG. 2A), receive reflected light of the emitted light, and convert the received reflected light into an electrical signal, thereby acquiring the first data. Based on the first data, it is possible to identify the user's heart rate, oxygen saturation, and/or blood pressure.

In operation 720, when executing the instructions, the processor may compare the first data obtained through the PPG sensor with reference data to identify whether the first data corresponds to the reference data. The reference data may be set based on an average heart rate of a person. According to an embodiment, the first data may include a change in the heart rate of the user for a unit time.

For example, the reference data may be set to be a heart rate of less than 60 beats per minute and greater than 80 beats per minute. The reference data may be a predetermined fixed value or a value determined differently depending on a user wearing the electronic device. The reference data may be adjusted by personal data such as e.g., physical age, physical characteristics, breathing habits, and/or presence or absence of respiratory diseases of a user who uses the electronic device 101. The processor may identify whether the user's heartbeats per minute corresponds to the above reference ranged, that is, less than 60 beats per minute or more than 80 beats per minute. When the user's heart rate is in a range between 60 and 80 beats per minute, the processor may be configured to perform the operation 710 again.

In operation 730, when executing the instructions, the processor may switch, based on identifying that the first data corresponds to the reference data, the at least one microphone (e.g., the microphone 600 of FIG. 2B) from an inactive state to an active state. For example, the processor may transmit a signal requesting transition from the inactive state to the active state to the at least one microphone, based on identifying that the first data corresponds to the reference data. Since the power consumption of the at least one microphone is relatively higher than that of the PPG sensor, the at least one microphone may maintain the inactive state until it is switched to the active state.

In operation 740, the processor may be configured to, when executing the instructions, acquire second data through the at least one microphone. The at least one microphone, while in the active state, may identify vibrations and/or sounds caused by air flowing through the user's nasal cavity. The at least one microphone may be disposed in a nose pad (e.g., the nose pad 410 of FIG. 2A) in contact with a part of the user's body. For example, the nose pad may be positioned adjacent to a nose of the user wearing the wearable device, and the at least one microphone may be arranged to face toward the user's nose in the nose pad.

In operation 750, when executing the instructions, the processor may identify at least one first audio signal generated from a part of the user's body of the second data obtained through the at least one microphone. For example, the processor may identify a first audio signal associated with a sound of the user's breathing generated from the user's nose. The processor may be configured to cancel noise except for at least one signal generated from a part of the user's body of the second data. For example, the processor may acquire a second audio signal around the electronic device from another microphone distinct from the at least one microphone. The processor may provide an inverse phase signal of the signal corresponding to noise of the second audio signal, in order to cancel noise caused by the second audio signal.

In operation 760, when executing the instructions, the processor may identify the user's breathing state, based on the identified at least one first audio signal. The processor may identify the user's breathing state, using a change in intensity of the audio signal, a period of the audio signal, and/or an acquisition interval of the audio signal. For example, the processor, when executing the instructions, may identify the user's respiration rate and a change in respiration rate, based on the change in intensity of the identified at least one audio signal. For another example, when executing the instructions, the processor may detect a respiration phase from an audio signal and may distinguish between an inhalation and an exhalation based on the detected respiration phase. When executing the instructions, the processor may detect a time interval of inhalation, a time interval of exhalation, an intensity of inhalation and exhalation, and/or a pause state between inhalation and exhalation. The processor may detect whether deep breathing is performed, based on the detected intensity of inhalation, and may estimate lung capacity through the deep breathing. For another example, when executing the instructions, the processor may detect cough, sneezing, stuffy nose, hiccups, hyperventilation, apnea and/or vomiting, based on the pause state between inhalation and exhalation, so as to detect any respiratory-related signs.

The user's breathing state identified by the processor may include at least one of the user's respiration rate, a change in respiration rate, a holding time of inhalation and exhalation, a time interval between inhalation and exhalation, a difference in breathing intensity between the left and right nasal cavities, or a time duration of the user's apnea.

Figure 8:
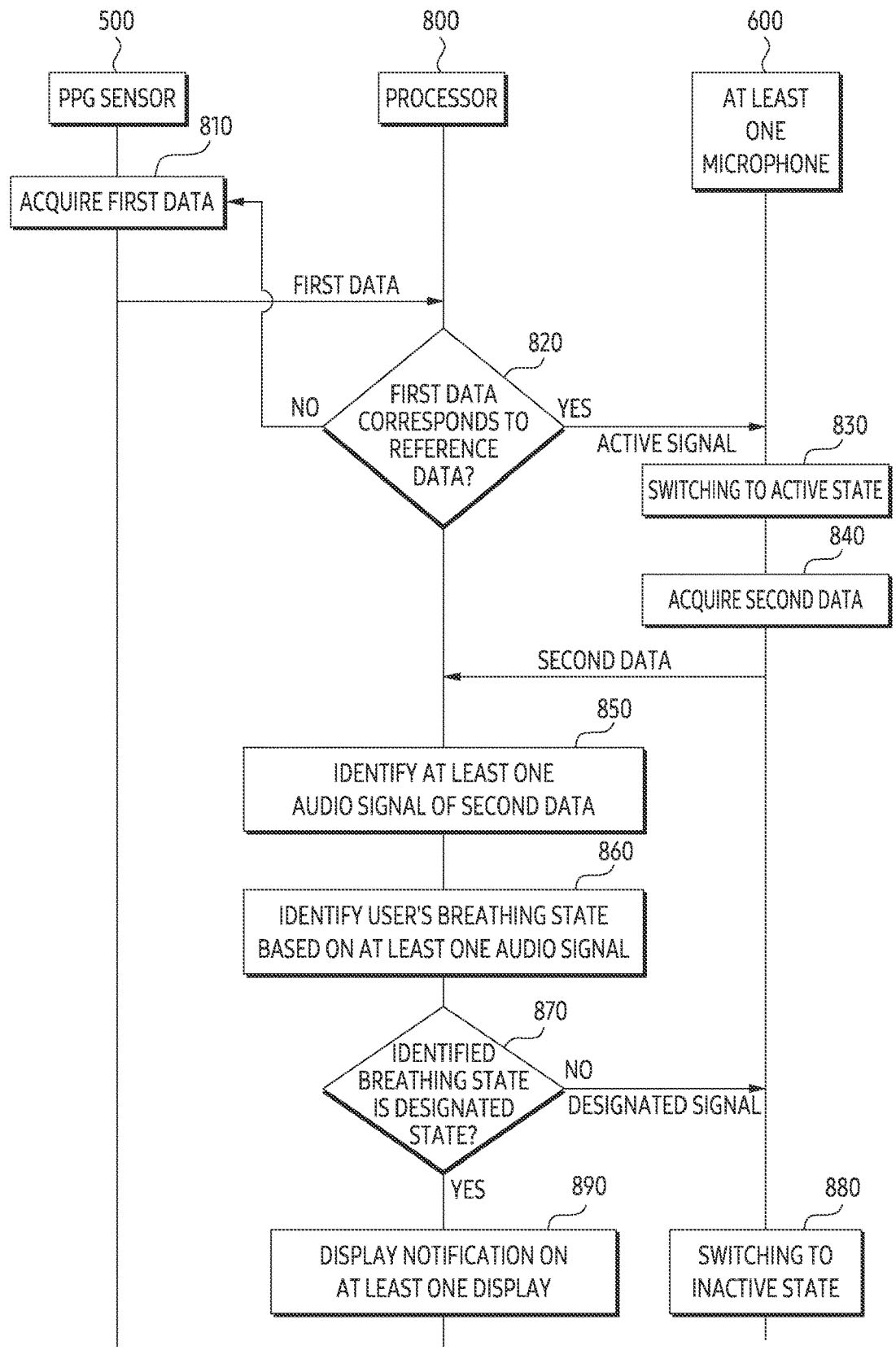
FIG. 8 illustrates an example of operations of an electronic device according to an embodiment of the disclosure.

FIG. 8 illustrates an example of operations of an electronic device according to an embodiment of the disclosure. The operation shown in FIG. 8 may be performed by the electronic device shown in FIGS. 2A and 2B (e.g., the electronic device 101 of FIG. 2A).

Referring to FIG. 8, in operation 810, the PPG sensor 500 may acquire first data. The PPG sensor 500 may initiate an operation in response to receiving a designated event. The PPG sensor 500 may acquire the first data by emitting light into the skin of the user wearing the electronic device, receiving reflected light of the emitted light, and converting the received reflected light into an electrical signal. The first data may include heart rate, oxygen saturation, and/or blood pressure. The PPG sensor 500 may transmit the obtained first data to the processor 800 (e.g., the processor 120 of FIG. 1).

In operation 820, when executing the instructions, the processor 800 may compare the first data obtained through the PPG sensor 500 with a reference data to identify whether the first data corresponds to the reference data. The operation 820 may correspond to the operation 720 of FIG. 7. When the first data corresponds to the reference data, the processor 800 may transmit an activation signal to at least one microphone 600 to convert the least one microphone 600 from an inactive state to an active state. The processor 800 may transmit a signal for switching the at least one microphone 600 from the inactive state to the active state directly to the at least one microphone 600, or request transmitting the signal via a power management module 188 (e.g., the power management module of FIG. 1) to the at least one microphone 600.

In operation 830, the at least one microphone 600 may be switched from the inactive state to the active state. The at least one microphone 600 may remain in the inactive state until it receives an activation signal from the processor 800. The active state may mean a mode in which the at least one microphone 600 operates to acquire second data while in a wake-up state. The inactive state may mean a turn-off state in which the at least one microphone 600 requests booting in order to switch to the wake-up state. The at least one microphone 600 may not consume any power in such an inactive state.

In operation 840, the at least one microphone 600 may acquire the second data for identifying the user's breathing state in the active state. For example, the at least one microphone 600 may acquire the second data through vibration and/or sound generated when the user breathes. The at least one microphone 600 may acquire the second data for a specified time duration from the activated timing. The at least one microphone 600 may transmit the obtained second data to the processor 800.

In operation 850, the processor 800 may identify at least one audio signal of the second data, when executing the instructions. The at least one audio signal may be an audio signal generated from a part of the user's body. For example, the at least one audio signal may be an audio signal related to a breathing sound generated from the user's nose. The operation 850 may correspond to the operation 750 of FIG. 7.

In operation 860, when executing the instructions, the processor 800 may identify the user's breathing state based on the identified at least one audio signal. The operation 860 may correspond to the operation 760 of FIG. 7. The user's breathing state identified by the processor 800 may include at least one of the user's respiration rate, a change in respiration rate, a holding time of inhalation and exhalation, a time interval between inhalation and exhalation, a difference in breathing intensity between the left and right nasal cavities, or a time duration of apnea of the user.

In operation 870, when executing the instructions, the processor 800 may identify whether the identified breathing state is a designated state. The designated state may mean a state distinguished from a common breathing state that may appear in a healthy user. For example, when the user's respiration rate is 12 to 20 breaths per minute, it may be identified as a normal breathing state, and when the user's respiration rate is less than 12 breaths per minute or more than 20 breaths, the processor 800 may identify that the breathing state is a designated state. As another example, when the apnea time in which the user does not breathe exceeds 20 seconds, the processor 800 may identify that the user's breathing state is a designated state. For another example, when the difference between the breathing intensities of the left nasal cavity and the right nasal cavity lasts for a specified time or longer, the processor 800 may identify that the user's breathing state is a designated state. The processor 800 may identify abnormal signs of the breathing state of which the user is not aware. When executing the instructions, the processor 800 may transmit a designated signal to the at least one microphone 600, based on identifying that the identified breathing state is not the designated state.

In operation 880, the at least one microphone 600 may be configured to be switched from the active state to the inactive state based on reception of the designated signal. By switching of the at least one microphone 600 from the active state to the inactive state, the electronic device 101 may minimize unnecessary power consumption.

The processor 800, when executing the instructions, may perform operation 890, based on identifying that the identified breathing state of the user is the designated state in operation 870.

In the operation 890, the processor 800, when executing the instructions, may be configured to display a notification related to the identified user's breathing state, through at least one display (e.g., the at least one display 300 of FIG. 2A). For example, the processor 800 may be configured to display a text, an image, and/or a video indicating the user's breathing state through at least one display. For example, when the number of the user's respirations rate per minute is less than 12 or more than 20, the processor 800 may display, through the at least one display, the number of the user's respiration rate per minute, and a warning text indicating that the breathing state is the designated state. A user wearing the electronic device may view a notification displayed on at least one display, and may obtain information on the user's breathing state through the notification. For example, in case of asthmatic patients, their cognitive ability for the breathing difficulties may be reduced, and thus the assessment of their respiratory status may be inaccurate. Those asthma patients can recognize that their breathing state is the designated state by means of the notification displayed on at least one display of the electronic device, and take any emergency action appropriate to the situation. For example, when a notification that the number of respirations per minute exceeds 20 is displayed on the at least one display, the user may decrease the breathing rate by stopping his/her motion and taking a rest. For another example, when it is displayed a notification indicating that the duration of apnea lasts for a predetermined time or more on at least one display, the user may stabilize his/her breathing state by taking a deep breath.

According to an embodiment, the electronic device may be configured to store data about a user in a memory (e.g., a memory 132 of FIG. 1). For example, the processor 800 may be configured to store data related to the identified user's breathing state in the memory, and the user may monitor the data related to the breathing state stored in the memory, thereby facilitating this/her better health management.

According to the above-described embodiment, the electronic device can identify the user's breathing state and provide the user with a notification, based on identifying that the identified breathing state is the designated state. The user wearing the electronic device can easily recognize his/her health conditions associated with the respiration. According to the above-described embodiment, the electronic device can provide the user with certain symptoms associated with various diseases related to the respiration (e.g., rhinitis, pneumonia, laryngitis, bronchitis, asthma, and so on).

The electronic device according to the above-described embodiment can improve a user's feelings of wearing, by disposing the PPG sensor 500 and the microphone 600 within a part of the frame (e.g., the frame 400 of FIG. 2A) in contact with the user's body. When a user wears a belt for measuring heart rate or a mask for measuring respiration on the chest for measuring the user's respiration, the user's movement may be restricted and thus, the user may feel uncomfortable. According to the above-described embodiment, the electronic device can make measurements of the user's respiration in a state of being worn by the user for another function distinguished from the respiration measurements, thereby enabling monitoring of the user's breathing state. For example, while the user is wearing the electronic device to view with augmented reality (AR), the electronic device can naturally measure the user's breathing state and then notify an abnormal symptom. According to an embodiment, the electronic device may provide such a notification through an external electronic device operatively connected to the electronic device. For example, the electronic device may provide a notification through an external electronic device connected via short-range communications (e.g., Wi-Fi or Bluetooth) under Internet of things (IoT) environment. The electronic device may provide the notification through an external electronic device connected with the same account in a server.

Figure 9:
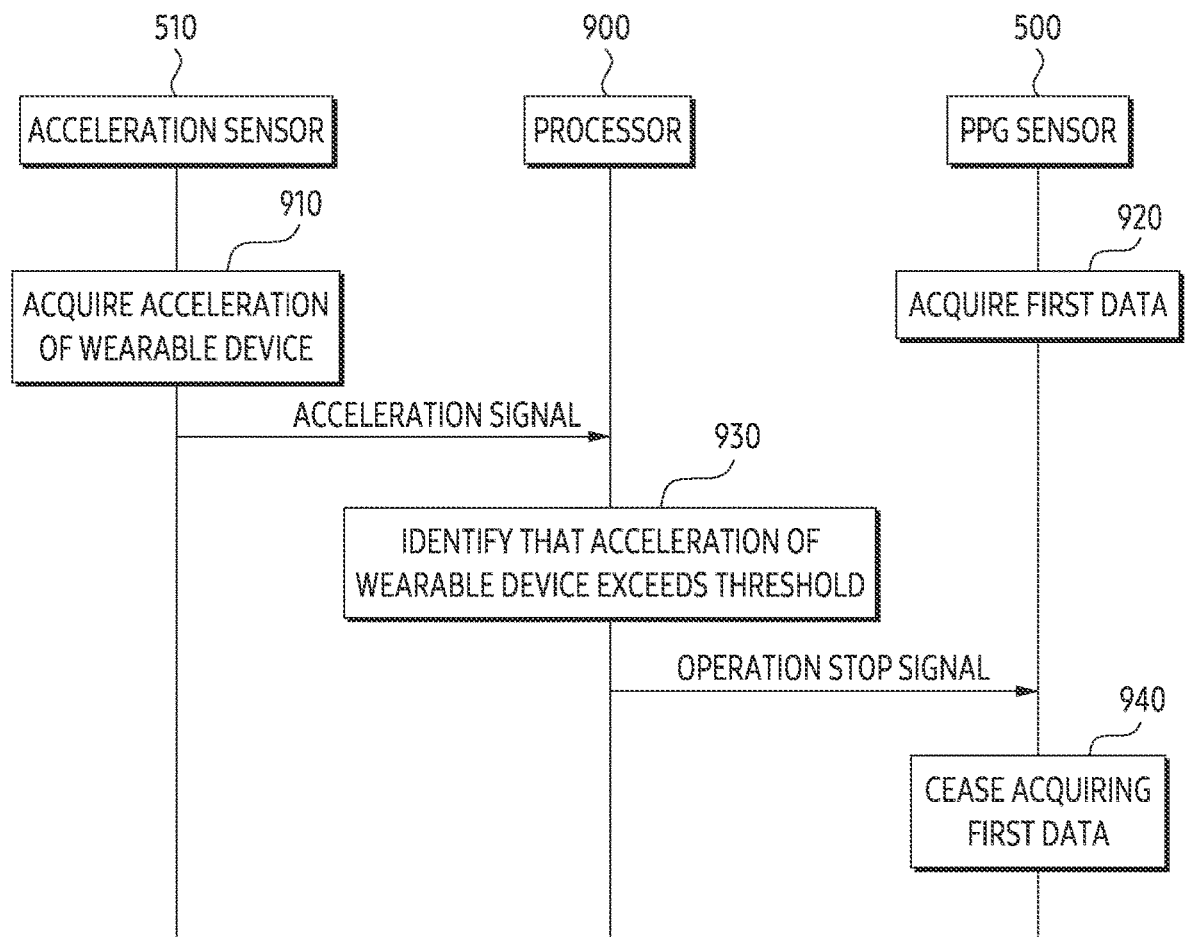
FIG. 9 illustrates an example of operations in which an operation of a PPG sensor is ceased based on an acceleration of an electronic device according to an embodiment of the disclosure.

FIG. 9 illustrates an example of operations in which the operation of the PPG sensor is stopped based on an acceleration of an electronic device according to an embodiment of the disclosure.

Referring to FIG. 9, an electronic device (e.g., the electronic device 101 of FIG. 2A) according to an embodiment may include an acceleration sensor 510 to identify a movement of the electronic device. In operation 910, the acceleration sensor 510 may identify a rate of change in speed with respect to each three-dimensional axis of the electronic device. The acceleration sensor 510 may identify an acceleration corresponding to each three-dimensional axis of the electronic device, and a processor 900 (e.g., the processor 120 of FIG. 1) may identify, based on the identified acceleration, a movement of the user wearing the electronic device. For example, when the acceleration of the electronic device obtained from the acceleration sensor 510 is greater than or equal to a predetermined value, the processor 900 may identify that the user wearing the electronic device is exercising. The acceleration sensor 510 may transmit an acceleration signal for the identified acceleration of the electronic device to the processor 900.

In operation 920, the PPG sensor 500 may identify first data. The PPG sensor 500 may initiate an operation in response to receiving a designated event. For example, in response to a user's designated gesture, the PPG sensor 500 may be configured to emit light into the user's body and detect reflected light for the emitted light. The operations 910 and 920 may be performed independently of each other.

In operation 930, the PPG sensor 500 may be configured to cease obtaining the first data, based on the acceleration data of the electronic device obtained from the acceleration sensor 510. The processor 900 may be configured to, based on the acceleration data of the electronic device obtained from the acceleration sensor 510, generate an operation stop signal causing the PPG sensor 500 to cease the operation and transmit the generated signal to the PPG sensor 500. For example, when executing the instructions, the processor 900 may be configured to, in response to the acceleration signal exceeding a designated threshold, either directly transmit the operation stop signal for the PPG sensor 500 to the PPG sensor 500, or transmit an operation stop command for the PPG sensor 500 via a printed circuit board 250 to the PPG sensor 500.

In operation 940, the PPG sensor 500 may be configured to, in response to receiving the operation stop signal, stop emitting light to the user's body and receiving reflected light of the emitted light. The PPG sensor 500 may cease obtaining the first data, and may be switched to an inactive state or turned off.

The PPG sensor 500 may be affected by a movement of the electronic device. The first data obtained from the PPG sensor 500 may be affected by motion noise generated by the user's movement. When the user moves while wearing the electronic device, an error in the first data may occur due to such motion noise. For example, when the user engages in vigorous exercise while wearing the electronic device, the accuracy of reflected light measured by the PPG sensor 500 is very low, and thus, substantially valid first data cannot be obtained. According to an embodiment, the electronic device may be configured to identify a situation that the PPG sensor 500 cannot obtain any substantially valid first data, based on the acceleration data obtained through the acceleration sensor by the user's movement, and cease the operation of the PPG sensor 500 under the situation, thereby preventing unnecessary power consumption.

Figure 10:
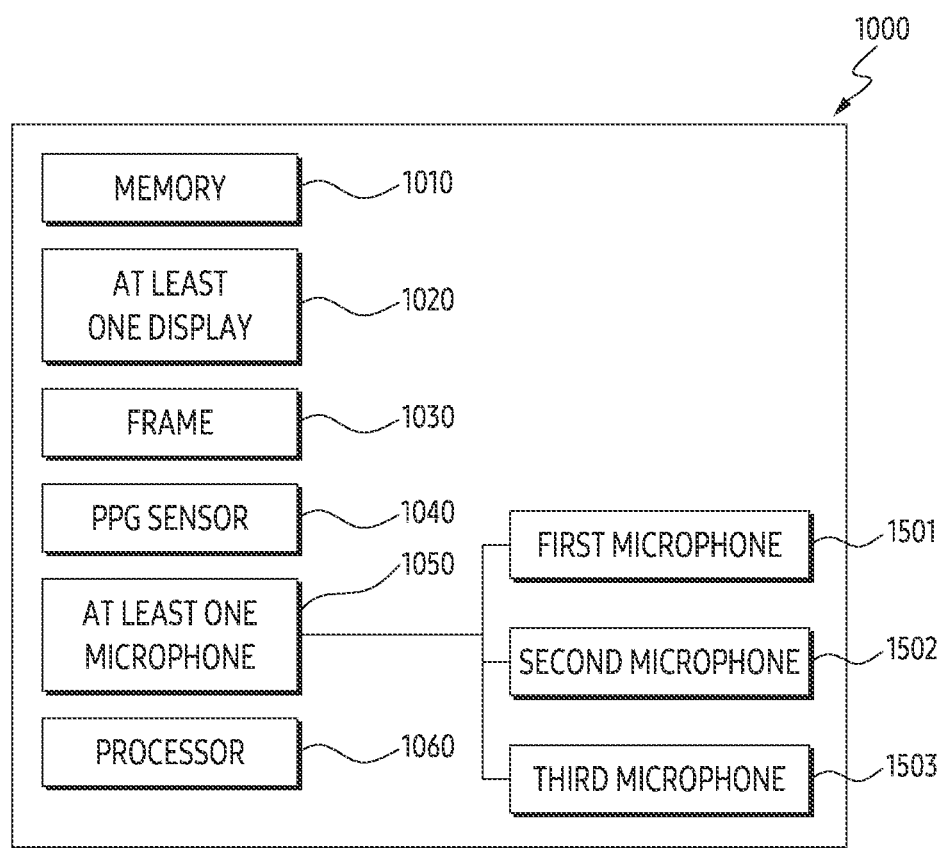
FIG. 10 is a block diagram of an electronic device according to an embodiment of the disclosure.

FIG. 10 is a block diagram of an electronic device according to an embodiment of the disclosure.

Referring to FIG. 10, according to an embodiment, an electronic device 1000 (e.g., an electronic device 101 of FIG. 2A) may include a memory 1010 (e.g., a memory 130 of FIG. 1) configured to store instructions, at least one display 1020 (e.g., at least one display 300 of FIG. 2A), a nose pad (e.g., a nose pad 410 of FIG. 2B), a frame 1030 (e.g., a frame 400 of FIG. 2A) configured to support the at least one display 1020, a PPG sensor 1040 (e.g., a PPG sensor 500 of FIG. 2B) exposed through at least a portion of the frame 1030, at least one microphone 1050 (e.g., at least one microphone 600 of FIG. 2B) disposed within the nose pad, and a processor 1060 (e.g., a processor 120 of FIG. 1).

According to an embodiment, the electronic device 1000 may be referred to as a wearable device that is worn on a part of a user's body. For example, the electronic device 1000 may be AR glasses worn on the user's face.

According to an embodiment, the memory may store instructions executed by the processor 1060. The instructions stored in the memory 1010 may be associated with a designated function of the electronic device 1000.

According to an embodiment, the at least one display 1020 may provide visual information to the user. The at least one display 1020 may be configured to cause light directed to a first surface (e.g., the first surface 301 of FIG. 2B) to be transmitted through a second surface (e.g., the second surface 302 of FIG. 2B) facing opposite to the first surface. The at least one display 1020 may display augmented reality, virtual reality, or mixed reality.

According to an embodiment, the frame 1030 may be configured to support the at least one display 1020. The at least one display 1020 may be worn on the user's body. The at least one display 1020 may come into contact with a part of the user's body when the user wears the electronic device 1000. For example, when the electronic device 1000 is worn by the user, the nose pad may be positioned adjacent to the user's nose.

According to an embodiment, the PPG sensor 1040 may be exposed through at least a portion of the frame 1030. The PPG sensor 1040 may use light to obtain a PPG signal through a change in blood flow in a micro-vessel. The PPG sensor 1040 may obtain the PPG signal based on emitting light to the user's body and detecting reflected light with respect to the emitted light.

According to an embodiment, the at least one microphone 1050 may be disposed in the nose pad to acquire audio signals. The at least one microphone 1050 may be arranged to face the user's body within the nose pad. For example, the at least one microphone 1050 may face the user's nose. The audio signals obtained from the at least one microphone 1050 may be obtained based on vibration and/or sound caused by air passing through a user's nasal cavity. Referring again to FIG. 10, the at least one microphone 1050 may include a first microphone 1501, a second microphone 1502, and a third microphone 1503. The first microphone 1501 and the second microphone 1502 may operate independently of each other. The first microphone 1501 and the second microphone 1502 may acquire audio signals at different positions, respectively. The third microphone 1503 may identify noise generated in any external environment of the electronic device 1000 and generate a sound wave to remove the noise. For example, the third microphone 1503 may include a removal unit to identify noise generated in the vicinity of the electronic device 1000 and analyze a phase of the identified noise, thereby generating a sound wave having an inverse phase of the analyzed phase.

The processor 1060 may execute instructions stored in the memory to control the overall operation of the electronic device 1000. The processor 1060 may be configured to receive data from the PPG sensor 1040 and the at least one microphone 1050 or control the operation of the PPG sensor 1040 and the at least one microphone 1050.

Figure 11:
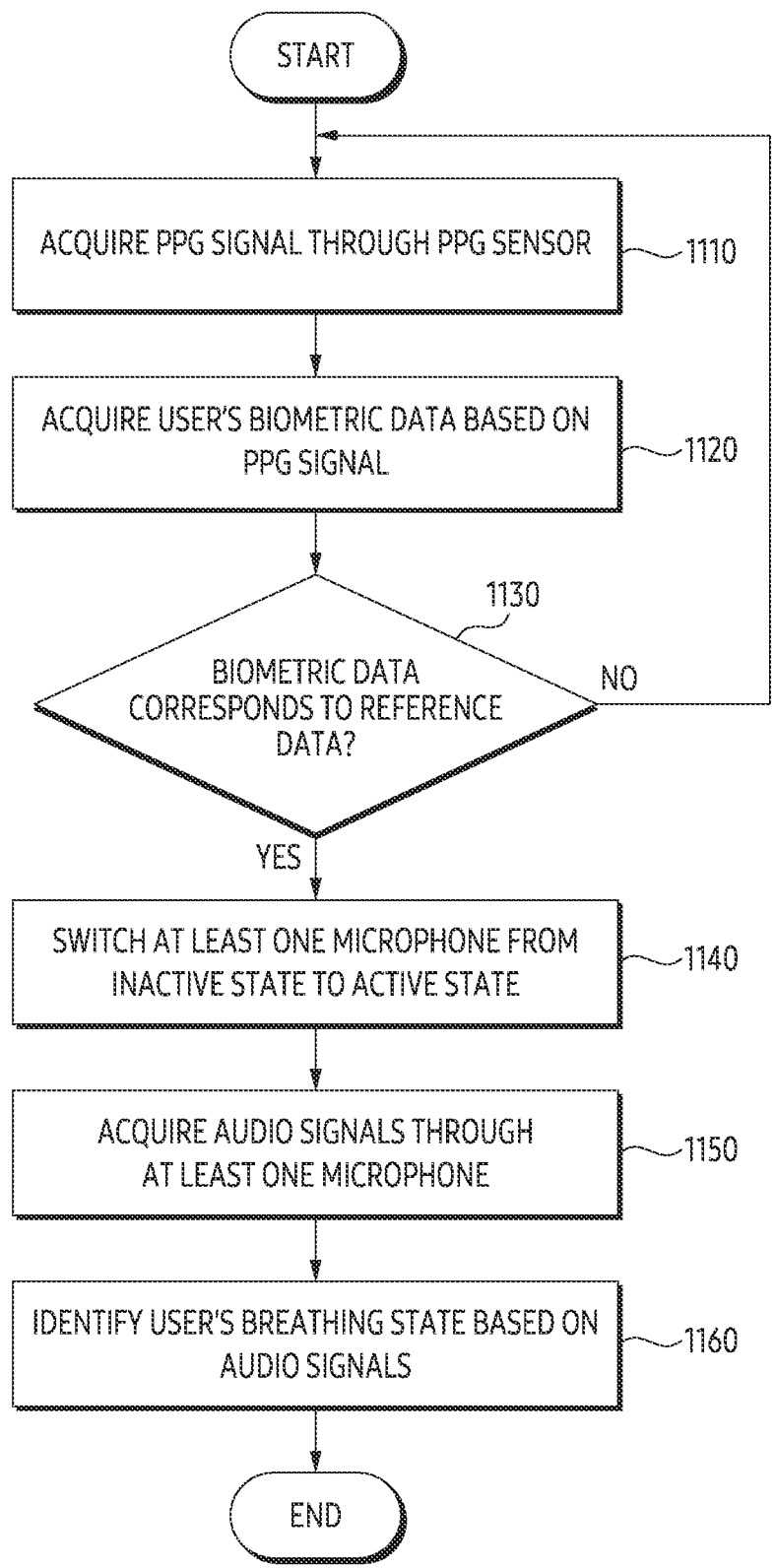
FIG. 11 is a flowchart illustrating an example of operations of a processor of an electronic device according to an embodiment of the disclosure.

FIG. 11 illustrates a flowchart for an example of operations of a processor of an electronic device according to an embodiment of the disclosure.

Referring to FIG. 11, in operation 1110, the processor (e.g., a processor 1060 of FIG. 10), when executing the instructions, may obtain a PPG signal through the PPG sensor (e.g., a PPG sensor 1040 of FIG. 10). The PPG signal may be an electrical signal obtained by converting reflected light from light emitted from the PPG sensor toward the user's body, into an electrical signal. The PPG signal may represent a waveform that changes over time due to a change in blood flow rate by a user's heart beating.

In operation 1120, the processor may obtain the user's biometric data, when executing the instructions. The processor may obtain the user's biometric data based on the PPG signal obtained through the PPG sensor. The processor may obtain the user's biometric data based on the waveform of the PPG signal. For example, the biometric data related to the user's respiration can be obtained based on a period of a signal obtained from the waveform of the PPG signal, a change in period, and/or its intensity. The biometric data may include a user's heart rate, a change in heart rate per a unit time, oxygen saturation, and/or blood pressure.

In operation 1130, when executing the instructions, the processor may compare the biometric data with reference data to identify whether the biometric data corresponds to the reference data. The reference data may be set based on an average heart rate of a person. For example, assuming that an average heart rate of a person is less than 60 beats per minute and more than 80 beats per minute, the reference data may be set to be less than 60 beats per minute and more than 80 beats per minute. When the user's heart rate per minute obtained based on the PPG signal is less than 60 beats per minute or exceeds 80 beats per minute, the processor may identify that the biometric data corresponds to the reference data.

In operation 1140, when executing the instructions, the processor may switch the at least one microphone (e.g., at least one microphone 1050 of FIG. 10) from an inactive state to an active state, based on identifying that the biometric data corresponds to the reference data. The at least one microphone may maintain the inactive state until it is switched to an active state. The at least one microphone may obtain, in the inactive state, power lower than the reference power from power management integrated circuit (PMIC) of the electronic device, and obtain power substantially equal to a reference power from the PMIC of the electronic device, when switching from the inactive state to the active state. When executing the instructions, the processor may transmit, to the at least one microphone, a signal to switch the at least one microphone from the inactive state to the active state.

In operation 1150, when executing the instructions, the processor may be configured to acquire audio signals via the at least one microphone. The at least one microphone, while in the active state, may obtain the audio signals related to the user's breathing and then transmit the obtained audio signals to the processor.

In operation 1160, when executing the instructions, the processor may identify a breathing state of the user based on the identified audio signals. The processor may identify the breathing state of the user, based on a change in intensity of the audio signal, a period of the audio signal, and/or an acquisition interval of the audio signal. For example, when executing the instructions, the processor may identify the user's breathing pattern from a period of the identified at least one audio signal.

Figure 12:
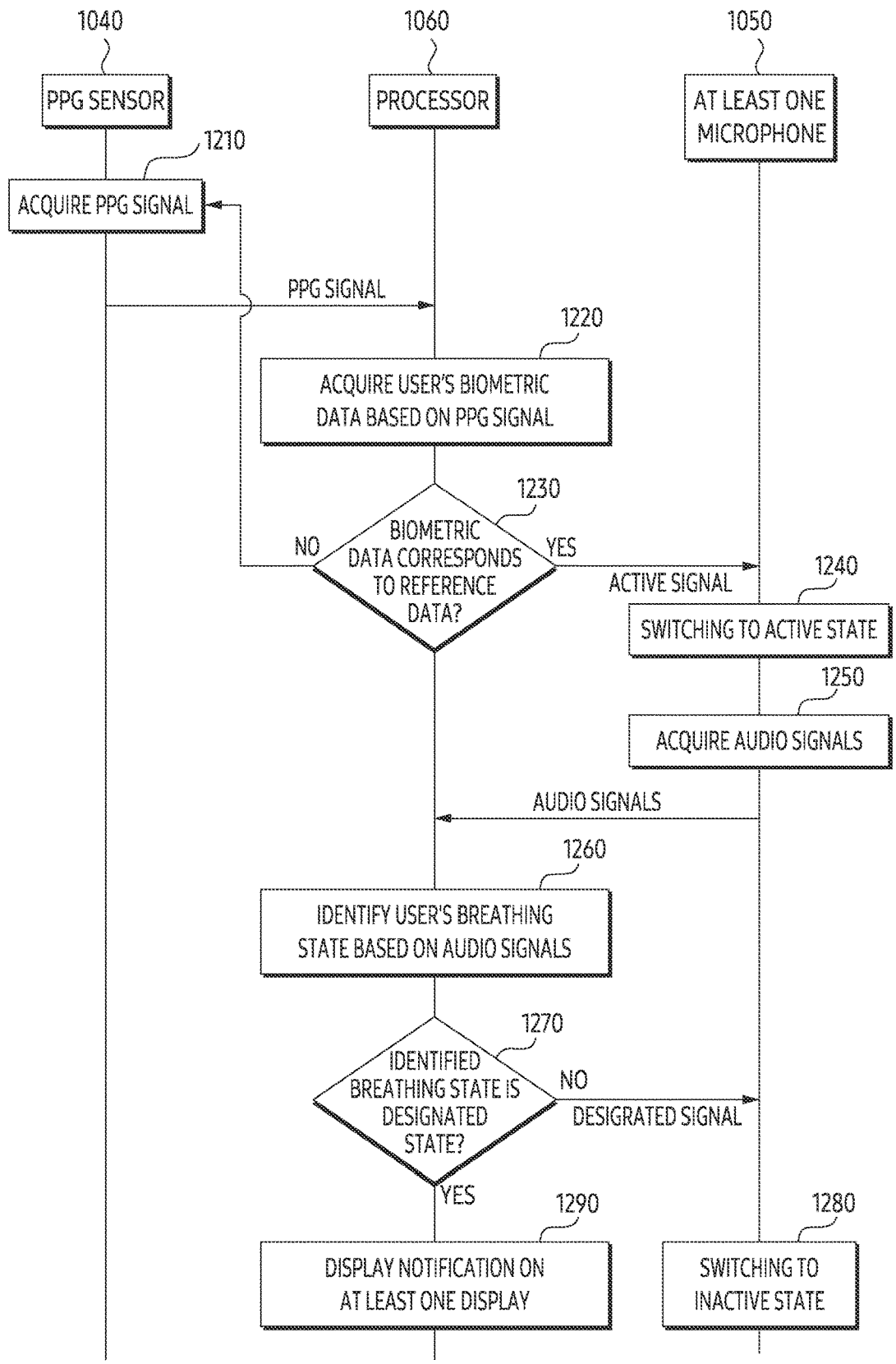
FIG. 12 illustrates an example of operation of an electronic device according to an embodiment of the disclosure.

FIG. 12 illustrates an example of an operation of an electronic device according to an embodiment of the disclosure. The operation illustrated in FIG. 12 may be performed by the electronic device (e.g., the electronic device 101) illustrated in FIGS. 2A and 2B or the electronic device (e.g., the electronic device 1000 of FIG. 10) illustrated in FIG. 10.

Referring to FIG. 12, in operation 1210, a PPG sensor 1040 (e.g., the PPG sensor 1040 of FIG. 10) may obtain a PPG signal. The PPG sensor 1040 may initiate an operation in response to receiving a designated event. The PPG sensor 1040 may obtain the PPG signal by emitting light into the skin of a user wearing the electronic device, receiving reflected light of the emitted light, and then converting the received reflected light into an electrical signal. The PPG sensor 1040 may transmit the obtained PPG signal to a processor 1060 (e.g., a processor 1060 of FIG. 10).

In operation 1220, when executing the instructions, the processor 1060 may obtain the user's biometric data based on the PPG signal. The operation 1220 may correspond to the operation 1120 of FIG. 11. The biometric data may be identified based on the waveform of the PPG signal.

In operation 1230, when executing the instructions, the processor 1060 may compare the obtained biometric data with reference data to identify whether the biometric data corresponds to the reference data. The operation 1230 may correspond to the operation 1130 of FIG. 11. When the biometric data corresponds to the reference data, the processor 1060 may transmit an activation signal for switching at least one microphone 1050 (e.g., the at least one microphone 1050 of FIG. 10) from an inactive state to an active state, to the at least one microphone 1050. The processor 1060 may transmit the activation signal for switching the at least one microphone 1050 from the inactive state to the active state, directly to the at least one microphone 1050, or request transmitting the activation signal to the at least one microphone 1050, via a power management module (e.g., a power management module 188 of FIG. 1).

In operation 1240, the at least one microphone 1050 may be switched from the inactive state to the active state. The at least one microphone 1050 may remain in the inactive state until it receives the activation signal from the processor 1060. The active state may refer to a mode in which the at least one microphone 1050 operates to acquire second data while in a wake-up state. The inactive state may refer to a mode in which the at least one microphone 1050 is in a sleep state distinct from the wake-up state.

In operation 1250, the at least one microphone 1050 may acquire audio signals for identifying the user's breathing state in the active state. For example, the at least one microphone 1050 may acquire the audio signals through vibration and/or sound generated when the user breathes. The at least one microphone 1050 may acquire the audio signals for a designated time duration from the activated time point. The at least one microphone 1050 may transmit the obtained audio signals to the processor 1060.

In operation 1260, the processor 1060, when executing the instructions, may identify the user's breathing state, based on the audio signals. The operation 1260 may correspond to the operation 1160 of FIG. 10. The user's breathing state identified by the processor 1060 may include at least one of the user's respiration rate, a change in respiration rate, a holding time of inhalation and exhalation, a time interval between inhalation and exhalation, a difference in breathing intensity between the left and right nasal cavities, or a duration time of apnea.

In operation 1270, when executing the instructions, the processor 1060 may identify whether the identified breathing state is a designated state. The designated state may stand for a state distinguished from a common breathing state that may appear in a healthy user. For example, when the user's respiration rate is 12 to 20 breaths per minute, it may be identified as a normal breathing state, and when the user's respiration rate is less than 12 breaths per minute or more than 20 breaths, the processor 1060 may identify the breathing state as the designated state. As another example, when the apnea duration time for which the user does not breathe exceeds 20 seconds, the processor 1060 may identify the user's breathing state as the designated state. As another example, when the difference in the breathing intensity between the left nasal cavity and the right nasal cavity lasts for more than a designated time, the processor 1060 may identify that the user's breathing state is the designated state. The processor 1060 may identify abnormal symptoms of the breathing state, of which the user is normally not aware for itself. When executing the instructions, the processor 1060 may transmit a designated signal to the at least one microphone 1050, based on identifying that the identified breathing state is not of the designated state.

In operation 1280, the at least one microphone 1050 may be configured to be switched from the active state to the inactive state, based on receiving the designated signal. As the at least one microphone 1050 is switched from the active state to the inactive state, the electronic device 1000 may minimize unnecessary power consumption.

The processor 1060, when executing the instructions, may perform operation 1290, based on identifying that the identified breathing state of the user is the designated state in operation 1270.

In operation 1290, when executing the instructions, the processor 1060 may be configured to display a notification related to the user's breathing state through the at least one display 1020. For example, the processor 1060 may be configured to display a phrase, a figure, and/or a moving picture indicating the user's breathing state through the at least one display 1020. For example, when the number of breathing per minute of the user is less than 12 or greater than 20, the processor 1060 may display, via at least one display (e.g., at least one display 1020 of FIG. 10), the number of breathing per minute of the user and a warning phrase that the breathing state is the designated state. The user wearing the electronic device 1000 may view a notification displayed on the at least one display, and may obtain information about the user's breathing state through the notification. For example, for asthmatic patients, their cognitive ability for any breathing difficulties may be reduced, and thus, the assessment of their breathing state may be inaccurate. Those asthma patients may recognize that their breathing state is the designated state through the notification displayed on the at least one display of the electronic device, and may take a certain remedy action appropriate to the situation. For example, when it is displayed on the at least one display a notification that the number of breathing per minute is greater than 20, the user may decrease the breathing rate by stopping his/her further motion and taking a rest. As another example, when a notification indicating that the time duration of apnea lasts for a predetermined time or more is displayed on at least one display, the user may take a deep breath to stabilize the breathing state.

According to an embodiment, the electronic device may be configured to store data about the user into a memory (e.g., the memory 1010 of FIG. 10). For example, the processor 1060 may be configured to store data related to the identified user's breathing state into the memory, and the user may facilitate health care by monitoring the data about the breathing state stored in the memory.

According to the above-described embodiment, the electronic device can identify the user's breathing state and provide the user with a notification, based on identifying that the identified breathing state is the designated state. The user wearing the electronic device may easily understand his/her health state related to breathing. According to the above-described embodiment, the electronic device can provide the user with symptoms related to various respiratory diseases related to breathing (e.g., rhinitis, pneumonia, laryngitis, bronchitis, asthma, and so on).

According to the above-described embodiment, the electronic device can improve power consumption efficiency. When an electronic device always maintains at least one microphone 1050 in an active state, its power consumption efficiency may be low due to the microphone consuming a relatively large amount of power. According to an embodiment, the electronic device may first obtain biometric data through the PPG sensor 1040 with relatively low power consumption, and the microphone 1050 with relatively high power consumption may be kept in an inactive state. According to an embodiment, when the biometric data corresponds to the reference data, the electronic device may acquire audio signals through the at least one microphone 1050 to identify the user's breathing state. According to an embodiment, the electronic device may identify whether or not a precise respiration measurement is required using the PPG sensor 1040, and when the precise respiration measurement is required, the electronic device can switch the at least one microphone 1050 to the active state, thereby improving its power consumption efficiency.

Figure 13:
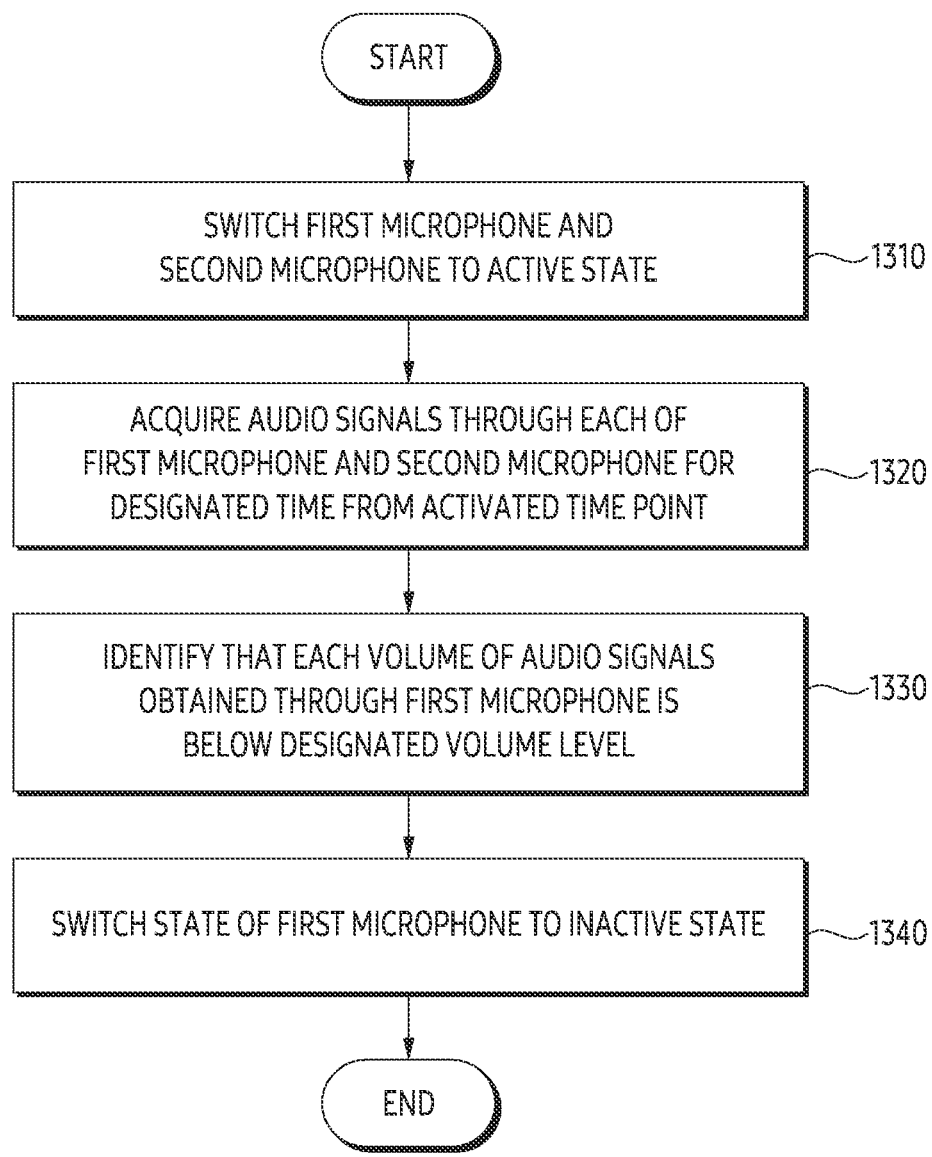
FIG. 13 is a flowchart illustrating an example of operations in which a processor of an electronic device controls at least one microphone, according to an embodiment of the disclosure.

FIG. 13 illustrates a flowchart for an example of operations in which a processor of an electronic device controls at least one microphone according to an embodiment of the disclosure.

According to an embodiment, the electronic device (e.g., the electronic device 1000 of FIG. 10) may acquire audio signals through each of a first microphone (e.g., the first microphone 1501 of FIG. 10) and a second microphone (e.g., the second microphones 1502 of FIG. 10). The first microphone and the second microphone may acquire the audio signals at different positions, respectively. The first microphone may be disposed in vicinity of the user's left nasal cavity to acquire the audio signals related to the user's left nasal cavity, and the second microphone may be disposed in vicinity of the user's right nasal cavity to acquire audio signals related to the user's right nasal cavity.

When the amount of respiration through both the nasal cavities of a user is not uniform, a difference may occur in audio signals obtained through the first microphone and the second microphone. For example, because the intensity of respiration through both nostrils may vary due to nasal cycle, the volume of the audio signal obtained through the first microphone is relatively very small, and the volume of the audio signal obtained through the second microphone may be sufficient. When the volume of the audio signal obtained through the first microphone is insufficient to identify the breathing state of the user wearing the electronic device, it may be not possible to identify the user's breathing state even though the first microphone is operating.

According to an embodiment, the processor (e.g., the processor 1060 of FIG. 10) may control operations of the first microphone and the second microphone in order to prevent unnecessary power consumption.

Referring to FIG. 13, in operation 1310, when executing the instructions, the processor may switch the first microphone and the second microphone from the inactive state to the active state. Such switching of the first microphone and the second microphone to the active state may be performed based on identifying that the biometric data corresponds to the reference data.

In operation 1320, the processor, when executing the instructions, may acquire the audio signals through each of the first microphone and the second microphone, for a designated time, from the time point at which each of the first microphone and the second microphone is activated. Each of the first microphone and the second microphone may be configured to identify audio signals originating from the user's body and transmit the identified audio signals to the processor. For example, the first microphone may acquire and transmit audio signals generated by respiration through the user's left nasal cavity to the processor, and the second microphone may acquire and transmit audio signals generated by respiration through the user's right nasal cavity. The first microphone and the second microphone may operate independently of each other. The designated time may be set to a time sufficient for the first microphone and the second microphone to acquire those audio signals.

In operation 1330, when executing the instructions, the processor may identify that the audio signals obtained through the first microphone are below a designated volume level. The designated volume may be a volume level to the extent that the user's breathing state cannot be identified, based on the audio signals obtained from the first microphone and the second microphone.

In operation 1340, the processor, when executing the instructions, may be configured to switch the state of the first microphone from the active state to the inactive state, based on identifying that the audio signals obtained through the first microphone are below the designated volume level. For example, in a cycle of the user breathing predominantly through the right nasal cavity and resting the left nasal cavity, the first microphone disposed on the left nasal cavity may not sufficiently obtain audio signals for identifying the user's breathing state. The processor can save power consumed for operating the first microphone by switching the first microphone, which fails to sufficiently acquire audio signals, from the active state to the inactive state. The state of the second microphone may be maintained independently of the switching of the first microphone from the active state to the inactive state. Even though the first microphone is switched from the active state to the inactive state, the second microphone can identify the audio signals, operating independently of the first microphone. According to the above-described embodiment, the electronic device can improve power consumption efficiency.

Figure 14:
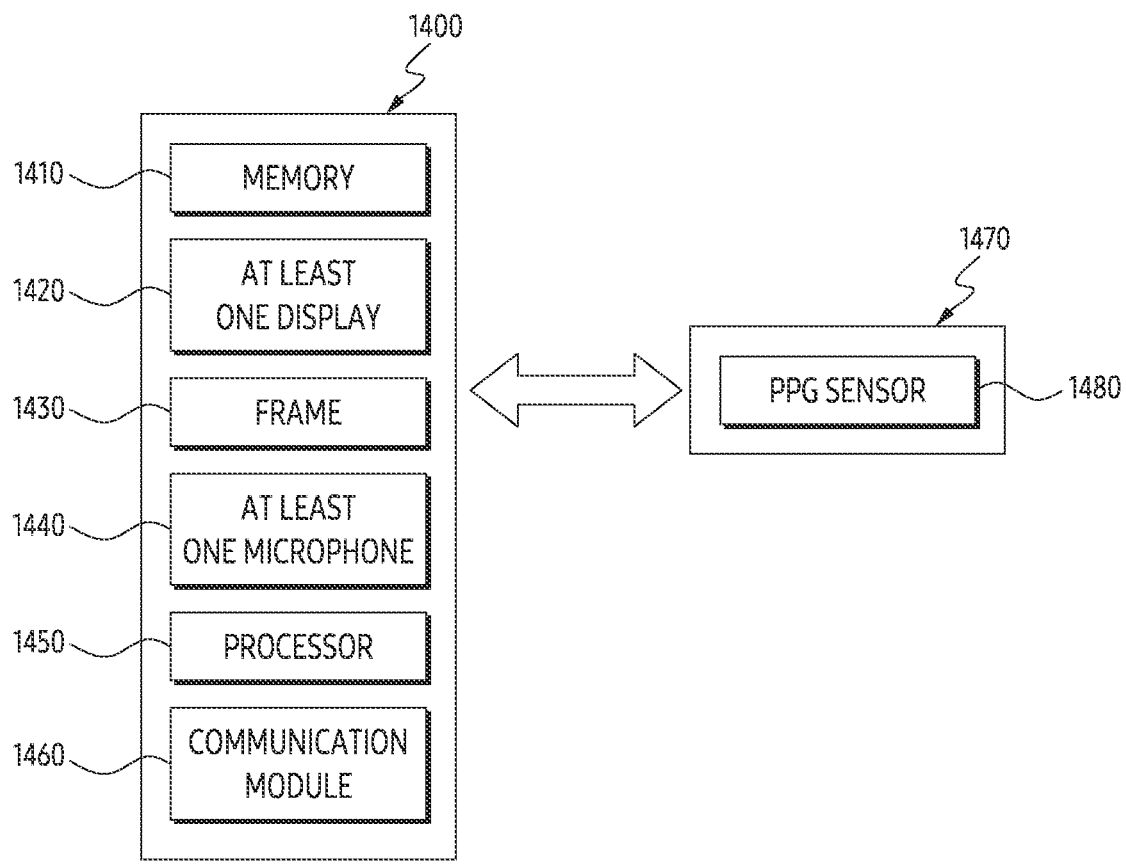
FIG. 14 is a block diagram of an electronic device and an external electronic device according to an embodiment of the disclosure.

FIG. 14 is a block diagram of an electronic device and an external electronic device, according to an embodiment of the disclosure.

Referring to FIG. 14, according to an embodiment, an electronic device 1400 (e.g., the electronic device 101 of FIG. 2A) may include a memory 1410 (e.g., the memory 130 of FIG. 1) configured to store instructions, at least one display 1420 (e.g., at least one display 300 of FIG. 2A), and a frame 1430 (e.g., the frame 400 of FIG. 2A) configured to support the at least one display 1420, at least one microphone 1440 (e.g., the at least one microphone 600 of FIG. 2B) to acquire audio signals related to the user's breathing, a processor 1450 (e.g., the processor 120 of FIG. 1), and a communication module 1460 (e.g., the communication module 190 of FIG. 1).

According to an embodiment, the communication module 1460 may be configured to support establishment of a direct communication channel or wireless communication channel between the electronic device 1400 and an external electronic device 1470, and performing communications through the established communication channel. The communication module 1460 may be referred to as the aforementioned communication module (e.g., the communication module 190 of FIG. 1). The communication module 1460 may transmit/receive data to and from the external electronic device 1470.

According to an embodiment, the electronic device 1400 and the external electronic device 1470 may be referred to as wearable devices. The user may wear both the electronic device 1400 and the external electronic device 1470 according to an embodiment. For example, according to an embodiment, the electronic device 1400 may be AR glasses, and the external electronic device 1470 may be a smart watch or a smart ring. The external electronic device 1470 may include a PPG sensor 1480 (e.g., the PPG sensor 500 of FIG. 2B) to identify the user's heart rate. The external electronic device 1470 may obtain a PPG signal related to the user's respiration through the PPG sensor 1480 and transmit the PPG signal to the communication module 1460. According to an embodiment, the electronic device 1400 may obtain a user's biometric data based on the PPG signal transmitted from the external electronic device 1470, and switch the at least one microphone 1440 from an inactive state to an active state, based on the obtained biometric data. At least one microphone 1440 may identify, in an active state, audio signals related to the user's respiration. The electronic device 1400 may be configured to identify a user's breathing state based on the identified audio signals, and display a notification through at least one display 1420 based on identifying that the identified breathing state is a designated state. According to an embodiment, the electronic device 1400 may transmit data about the user's breathing state to another external electronic device (e.g., a smart phone or a tablet personal computer (PC)) through the communication module 1460. According to an embodiment, the electronic device 1400 may provide a notification of the breathing state via another external electronic device connected over short-range communication (e.g., Wi-Fi or Bluetooth) in IoT environment. The electronic device 1400 may provide the notification through another external electronic device connected to the same account in a server.

According to an embodiment, a wearable device may include a memory (e.g., a memory 130 of FIG. 1) configured to store instructions; at least one display (e.g., at least one display 300 of FIG. 2A) configured to transmit light directed to a first surface (e.g., a first surface 301 of FIG. 2B) through a second surface (e.g., a second surface 302 of FIG. 2B), the second surface facing opposite to the first surface, the at least one display including a display area on the first surface or the second surface; a frame (e.g., frame 400 of FIG. 2A) configured to support the at least one display, the frame including a nose pad (e.g., a nose pad 410 of FIG. 2A) in contact with a part of a user's body wearing the wearable device; a PPG sensor (e.g., a PPG sensor 500 of FIG. 2B) exposed through at least a portion of the frame in contact with another part of the user's body; at least one microphone (e.g., at least one microphone 600 of FIG. 2B) disposed in the nose pad; and a processor (e.g., a processor 120 of FIG. 1). The processor, when executing the instructions, may be configured to identify a breathing state of the user, based at least in part on first data acquired through the PPG sensor or second data acquired through the at least one microphone According to an embodiment, the first data may include a change in the user's heart rate per unit time.

According to an embodiment, the nose pad may be configured to be in contact with a nose of the user wearing the wearable device, and the at least one microphone may face the user's nose in the nose pad.

According to an embodiment, the processor, when executing the instructions, may be further configured to switch a state of the at least one microphone from an inactive state to an active state, based on identifying that the first data corresponds to reference data while the at least one microphone is in the inactive state.

According to an embodiment, the processor, when executing the instructions, may be further configured to identify at least one audio signal generated from the part of the user's body of the second data, and identify the breathing state based on the at least one audio signal.

According to one embodiment, the breathing state may comprise at least one of the user's breathing rate per unit time, a change in the user's breathing rate, a duration of the user's inhalation and exhalation, a time interval between the user's inhalation and exhalation, a difference in breathing intensity between the user's left and right nasal cavities, or a duration of the user's apnea.

According to an embodiment, the processor, when executing the instructions, may be further configured to identify whether the identified breathing state is a designated state, and display a notification through the at least one display, based on identifying that the identified breathing state is the designated state.

According to an embodiment, the at least one display may comprise a first display (e.g., a first display 310 of FIG. 2A) and a second display (e.g., a second display 320 of FIG. 2A) spaced apart from the first display, the frame may comprise a first rim (e.g., a first rim 401 of FIG. 2A) surrounding at least a portion of the first display, a second rim (e.g., a second rim 402 of FIG. 2A) surrounding at least a portion of the second display, a bridge (e.g., a bridge 403 of FIG. 2B) disposed between the first rim and the second rim, a first pad (e.g., a first pad 411 of FIG. 2A) disposed along a portion of an edge of the first rim from an end of the bridge, and a second pad (e.g., a second pad 412 of FIG. 2A) disposed along a portion of an edge of the second rim from another end of the bridge. The at least one microphone comprises a first microphone (e.g., a first microphone 610 of FIG. 2B) disposed in the first pad and a second microphone (e.g., a second microphone 620 of FIG. 2B) disposed in the second pad.

According to an embodiment, the processor, when executing the instructions, may be further configured to acquire the second data through each of the first microphone and the second microphone for a designated time from a time point when each of the first microphone and the second microphone are activated.

According to an embodiment, the processor, when executing the instructions, may be further configured to acquire audio signals by cancelling noise included in second data.

According to an embodiment, the frame may comprise rims supporting the at least one display and temples extending from the rims to be disposed on the other part of the user's body, and the PPG sensor may be exposed through at least a part of the temples in contact with the other part of the user's body.

According to an embodiment, the wearable device may further comprise an acceleration sensor configured to identify a movement of the wearable device, and the PPG sensor may be configured to stop acquiring the first data, based on the movement of the wearable device acquired through the acceleration sensor.

According to an embodiment, a wearable device (e.g., an electronic device 1000 of FIG. 10) may comprise a memory (e.g., a memory 1010 of FIG. 10) configured to store instructions; at least one display (e.g., at least one display 1020 of FIG. 10) configured to transmit light directed to a first surface (e.g., a first surface 301 of FIG. 2B) through a second surface (e.g., a second surface 302 of FIG. 2B), the second surface facing opposite to the first surface, the at least one display including a display area on the first surface or the second surface; a frame (e.g., a frame 1030 of FIG. 10) configured to support the at least one display, the frame including a nose pad (e.g., a nose pad 410 of FIG. 2A); a PPG sensor (e.g., a PPG sensor of FIG. 10) exposed through at least a portion of the frame; at least one microphone (e.g., at least one microphone 1050 of FIG. 10) disposed in the nose pad; and a processor (e.g., a processor 1060 of FIG. 10). The processor, when executing the instructions, may be configured to acquire a PPG signal through the PPG sensor while the at least one microphone is in an inactive state, acquire biometric data of a user wearing the wearable device, based on the PPG signal, switch a state of the at least one microphone from the inactive state to an active state, based on identifying that the biometric data corresponds to reference data, acquire audio signals through the at least one microphone switched to the active state, and identify a breathing state of the user based on the audio signals.

According to an embodiment, the biometric data may comprise a change in the user's heart rate per unit time, and the processor, when executing the instructions, may be further configured to switch the state of the at least one microphone from the inactive state to the active state, based on identifying that the change in the user's heart rate per unit time corresponds to a designated threshold.

According to an embodiment, the processor, when executing the instructions, may be further configured to identify the breathing state based on the audio signals.

According to an embodiment, the processor, when executing the instructions, may be further configured to identify whether the identified breathing state is a designated state, and display a notification through the at least one display, based on identifying that the identified breathing state is the designated state.

According to an embodiment, the at least one microphone may comprise a first microphone (e.g., a first microphone 1501 in FIG. 10) disposed at one end of the nose pad and a second microphone (e.g., a second microphone 1502 of FIG. 10) disposed at the other end of the nose pad, wherein the processor, when executing the instructions, may be further configured to acquire the audio signals through each of the first microphone and the second microphone for a designated time from a time point when each of the first microphone and the second microphone is activated, identify that a volume of the audio signals acquired through the first microphone is less than a designated volume, and switch a state of the first microphone to the inactive state, based on identifying that the volume is less than the designated volume.

According to an embodiment, the state of the second microphone may be maintained independently of switching the state of the first microphone to the inactive state.

According to an embodiment, the wearable device may further comprise an acceleration sensor (e.g., an acceleration sensor 510 of FIG. 2B) to identify a movement of the wearable device, wherein the PPG sensor may be configured to cease acquiring the biometric data, based on identifying the movement of the wearable device exceeding a predetermined threshold from the acceleration sensor.

According to an embodiment, the processor, when executing the instructions, may be further configured to acquire other audio signals by canceling noise included in each of the audio signals.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment, the electronic devices are not limited to those described above.

It should be appreciated that various embodiments and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may be interchangeably used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., an internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable device comprising:
   memory including one or more storage media storing instructions;
   at least one display, when the wearable device is worn by a user, positioned in front of eyes of the user;
   a frame configured to support the at least one display, the frame including a nose pad contacted with a part of a body of the user, when the wearable device is worn;
   a photoplethysmography (PPG) sensor in the frame, contacted with another part of the body of the user, when the wearable device is worn;
   at least one microphone; and
   at least one processor including processing circuitry,
   wherein the instructions, when executed by the at least one processor individually or collectively, cause the wearable device to:
      while identifying a respiration of the user wearing the wearable device, through the at least one microphone, is deactivated, identify a first data associated with the respiration of the user through the PPG sensor, and
      based on the first data reaching threshold data, activate identifying the respiration of the user through the at least one microphone for identifying second data associated with the respiration of the user.

2. The wearable device of claim 1, wherein the activating the identifying the respiration of the user through the at least one microphone by switching a state of the at least one microphone from a first state providing a first power to the at least one microphone to a second state providing a second power higher than the first power to the at least one microphone.

3. The wearable device of claim 1,
wherein the at least one microphone is disposed in the nose pad of the frame,
wherein the nose pad is contacted with a nose of the user, when the wearable device is worn, and
wherein the at least one microphone in the nose pad of the frame faces the nose of the user in the nose pad.

4. The wearable device of claim 1,
wherein the second data comprise at least one audio signal caused by a part of the body of the user, and
wherein the instructions, when executed by the at least one processor individually or collectively, cause the wearable device to:
identify the at least one audio signal of the second data, and
identify a breathing state based on the at least one audio signal.

5. The wearable device of claim 1, wherein the instructions, when executed by the at least one processor individually or collectively, cause the wearable device to:
identify the second data associated with the respiration of the user through the at least one microphone, and
identify a breathing state of the user based on the second data.

6. The wearable device of claim 5, wherein the instructions, when executed by the at least one processor individually or collectively, cause the wearable device to:
identify whether the identified breathing state is a designated state, and
display a notification through the at least one display, based on identifying that the identified breathing state is the designated state.

7. The wearable device of claim 1,
wherein the at least one display comprises:
a first display, and
a second display spaced apart from the first display,
wherein the frame comprises:
a first rim surrounding at least a portion of the first display,
a second rim surrounding at least a portion of the second display,
a bridge disposed between the first rim and the second rim,
a first pad disposed along a portion of an edge of the first rim from one end of the bridge, and
a second pad disposed along a portion of an edge of the second rim from another end of the bridge, and
wherein the at least one microphone comprises:
a first microphone disposed in the first pad, and
a second microphone disposed in the second pad.

8. The wearable device of claim 7, wherein the instructions, when executed by the at least one processor individually or collectively, cause the wearable device to:
identify the second data through each of the first microphone and the second microphone for a designated time from a time point, when the first microphone and the second microphone are each activated.

9. The wearable device of claim 1, wherein the instructions, when executed by the at least one processor individually or collectively, cause the wearable device to:
obtain audio signals by cancelling noise included in second data.

10. The wearable device of claim 1,
wherein the frame comprises:
rims supporting the at least one display, and
temples extending from the rims to be disposed on the other part of the body of the user, and
wherein the PPG sensor is exposed through at least a part of the temples contacted with the other part of the body of the user.

11. The wearable device of claim 1, further comprising:
an acceleration sensor configured to identify a movement of the wearable device,
wherein the PPG sensor is configured to stop obtaining the first data, based on the movement of the wearable device obtained through the acceleration sensor.

12. A wearable device comprising:
memory including one or more storage media storing instructions;
at least one display configured to transmit light directed to a first surface through a second surface, the second surface facing opposite to the first surface, the at least one display including a display area on the first surface or the second surface;
a frame configured to support the at least one display, the frame including a nose pad;
a photoplethysmography (PPG) sensor disposed in the frame;
at least one microphone disposed in the nose pad; and
at least one processor;
wherein the instructions, when executed by the at least one processor individually or collectively, cause the wearable device to:
identify a PPG signal through the PPG sensor, while the at least one microphone is in an inactive state,
identify biometric data of a user wearing the wearable device, based on the PPG signal,
switch a state of the at least one microphone from the inactive state to an active state, based on the biometric data reaching a threshold data,
identify audio signals through the at least one microphone switched to the active state, and
identify a breathing state of the user based on the audio signals, and
wherein a power consumption of the PPG sensor is lower than a power consumption of the at least one microphone.

13. The wearable device of claim 12,
wherein the biometric data comprises a change in heart rate of the user, and
wherein the instructions, when executed by the at least one processor individually or collectively, cause the wearable device to:
switch the state of the at least one microphone from the inactive state to the active state, based on identifying that the change in the heart rate of the user corresponds to a designated threshold.

14. The wearable device of claim 12, wherein the instructions, when executed by the at least one processor individually or collectively, cause the wearable device to:
identify whether the identified breathing state is a designated state, and
display a notification through the at least one display based on identifying that the identified breathing state is the designated state.

15. The wearable device of claim 12,
wherein the at least one microphone comprises:

a first microphone disposed at one end of the nose pad, and a second microphone disposed at another end of the nose pad, and wherein the instructions, when executed by the at least one processor individually or collectively, cause the wearable device to:

identify the audio signals through each of the first microphone and the second microphone for a designated time from a time point when each of the first microphone and the second microphone is activated, identify that a volume of the audio signals identified through the first microphone is less than a designated volume, and switch a state of the first microphone to the inactive state, based on identifying that the volume is less than the designated volume.

16. The wearable device of claim 15, wherein the state of the second microphone is maintained independently of switching the state of the first microphone to the inactive state.

17. The wearable device of claim 12, further comprising:
an acceleration sensor configured to identify a movement of the wearable device, wherein the PPG sensor is configured to stop identifying the PPG signal, based on the movement of the wearable device identified through the acceleration sensor exceeding a designated threshold.

18. The wearable device of claim 12, wherein the instructions, when executed by the at least one processor individually or collectively, cause the wearable device to;
obtain other audio signals by canceling noise included in each of the audio signals.

19. The wearable device of claim 2,
wherein the first state of the at least one microphone includes an inactive state of the at least one microphone, and wherein the second state of the at least one microphone includes an active state of the at least one microphone.

20. The wearable device of claim 5, wherein the breathing state comprises at least one of the user's-breathing rate of the user, a change in the breathing rate of the user, a duration of inhalation and exhalation of the user, a time interval between the inhalation and exhalation of the user, a difference in breathing intensity between left and right nasal cavities of the user, or a duration of apnea of the user.

* * * * *